United States Patent
Figg et al.

(10) Patent No.: US 10,094,836 B2
(45) Date of Patent: Oct. 9, 2018

(54) SLCO1B3 GENOTYPE

(75) Inventors: William D. Figg, Fairfax, VA (US);
Alex Sparreboom, Memphis, TN (US);
Akinobu Hamada, Tokyo (JP);
Douglas K. Price, Fairfax, VA (US);
Tristan M. Sissung, Annandale, VA (US)

(73) Assignee: The United States of America, as represented by the Secretary, Department of Health & Human Services, Washington, DC (US)

( * ) Notice: Subject to any disclaimer, the term of this patent is extended or adjusted under 35 U.S.C. 154(b) by 894 days.

(21) Appl. No.: 12/522,480

(22) PCT Filed: Jan. 8, 2008

(86) PCT No.: PCT/US2008/000310
§ 371 (c)(1),
(2), (4) Date: Aug. 26, 2010

(87) PCT Pub. No.: WO2008/086002
PCT Pub. Date: Jul. 17, 2008

(65) Prior Publication Data
US 2010/0317726 A1    Dec. 16, 2010

Related U.S. Application Data

(60) Provisional application No. 60/879,503, filed on Jan. 8, 2007.

(51) Int. Cl.
*C12Q 1/68*     (2018.01)
*G01N 33/574*   (2006.01)
*C12Q 1/6886*   (2018.01)

(52) U.S. Cl.
CPC ..... *G01N 33/57434* (2013.01); *C12Q 1/6886* (2013.01); *C12Q 2600/106* (2013.01); *C12Q 2600/118* (2013.01); *C12Q 2600/136* (2013.01); *C12Q 2600/172* (2013.01)

(58) Field of Classification Search
None
See application file for complete search history.

(56) References Cited

U.S. PATENT DOCUMENTS

| | | | |
|---|---|---|---|
| 4,342,566 A | 8/1982 | Theofilopoulos et al. | |
| 4,683,195 A | 7/1987 | Mullis et al. | |
| 4,683,202 A | 7/1987 | Mullis | |
| 4,704,692 A | 11/1987 | Ladner | |
| 4,814,470 A | 3/1989 | Colin et al. | |
| 4,816,567 A | 3/1989 | Cabilly et al. | |
| 4,965,188 A | 10/1990 | Mullis et al. | |
| 5,225,539 A | 7/1993 | Winter | |
| 5,438,072 A | 8/1995 | Bobbee et al. | |
| 5,545,806 A | 8/1996 | Lonberg et al. | |
| 5,569,825 A | 10/1996 | Lonberg et al. | |
| 5,625,126 A | 4/1997 | Lonberg et al. | |
| 5,633,425 A | 5/1997 | Lonberg et al. | |
| 5,661,016 A | 8/1997 | Lonberg et al. | |
| 5,698,582 A | 12/1997 | Bastart et al. | |
| 5,714,512 A | 2/1998 | Bastart et al. | |
| 5,804,440 A | 9/1998 | Burton et al. | |
| 6,096,551 A | 8/2000 | Barbas et al. | |
| 2003/0073096 A1* | 4/2003 | Bao et al. | 435/6 |
| 2003/0215805 A1* | 11/2003 | Lillie et al. | 435/6 |
| 2004/0072156 A1 | 4/2004 | Nakamura et al. | |
| 2004/0121371 A1 | 6/2004 | Andersen et al. | |
| 2005/0163821 A1 | 7/2005 | Sung et al. | |
| 2005/0165352 A1 | 7/2005 | Henry et al. | |
| 2005/0165474 A1 | 7/2005 | Majercak et al. | |
| 2005/0169969 A1 | 8/2005 | Li et al. | |
| 2005/0171593 A1 | 8/2005 | Whirley et al. | |
| 2005/0171597 A1 | 8/2005 | Boatman et al. | |
| 2005/0171598 A1 | 8/2005 | Schaeffer et al. | |
| 2005/0171599 A1 | 8/2005 | White | |
| 2005/0177246 A1 | 8/2005 | Datta et al. | |

FOREIGN PATENT DOCUMENTS

| | | |
|---|---|---|
| EP | 0125023 | 11/1984 |
| EP | 0171496 | 2/1986 |
| EP | 0173494 | 5/1986 |
| EP | 0184187 | 11/1986 |
| EP | 1 277 843 A2 | 1/2003 |
| WO | WO 1986/001533 | 3/1986 |
| WO | WO 1987/002671 | 5/1987 |
| WO | WO 1994/029348 | 12/1994 |
| WO | 03/106709 A1 | 12/2003 |

OTHER PUBLICATIONS

NM_001032941.1 [online][retrieved on Sep. 5, 2012] retrieved from: http://www.ncbi.nlm.nih.gov/nuccore/nm_001032941.*
NM_019844.3 [online][retrieved on Sep. 5, 2012] retrieved from: http://www.ncbi.nlm.nih.gov/nuccore/nm_019844.*
AJ251506.1 [online][retrieved on Sep. 5, 2012] retrieved from http://www.ncbi.nlm.nih.gov/nuccore/aj251506.*
NG_032071.1 [online][retrieved on Sep. 5, 2012] retrieved from http://www.ncbi.nlm.nih.gov/nuccore/375298755?report=fasta&from=5001&to=111208.*
Petrylak, D. Therapeutic options in androgen-independent prostate cancer: building on docetaxel. BJU International 96(s2):41-46, Dec. 2005.*
Smith et al. Role of the liver-specific transporters OATP1B1 and OATP1B3 in governing drug elimination. Expert Opin. Drug Metab. Toxicol. 1(3):429-445 (2005).*
Petrylak et al. The New England Journal of Medicine 351(15):1513-1520 (Year: 2004).*

(Continued)

*Primary Examiner* — Samuel C Woolwine
(74) *Attorney, Agent, or Firm* — Locke Lord LLP; Nicholas J. DiCeglie, Jr.

(57) ABSTRACT

The invention relates methods of identifying and predicting inter-patient differences in prognostic prediction for survival in androgen independent prostate cancer. It further related to methods for determining and exploiting such differences to improve medical outcomes. Moreover, it provides methods for determining if a subject has prostate cancer.

3 Claims, 4 Drawing Sheets
Specification includes a Sequence Listing.

(56) References Cited

OTHER PUBLICATIONS

Abe et al., Gastroenterology, 120:1689-1699 (2001).
Hamada et al., Clinical Cancer Research: an Official Journal of the American Associate for Cancer Research, 14(11):3312-3318 (2008).
Hedelin et al., Prostate, 66(14):1512-1520 (2006).
Letschert et al., Pharmacogenetics, 14(7):441-452 (2004).
Muto et al., Cancer Science, 98(10):1570-1576 (2007).
Nishizato et al., Clinical Pharmacology & Therapeutics, 73(6):554-565 (2003).
Tsujimoto et al., Drug Metab. Pharmacokinet, 21(2):SNP8(165)-SNP12(169) (2006).
Smith et al., Clinical Pharmacology & Therapeutics, 81:76-82 (2007).
Bowden, et al., "A phase I/II study of continuous infusion suramin in patients with hormone-refratory prostate cancer: toxicity and response." Cancer Chemother Pharmacol; 39: 1-8 (1996).
Cicek, et al., "Role of androgen metabolism genes CYP1B1, PSA/KLK3, and CYP11 alpha in prostate cancer risk and aggressiveness." Cancer Epidemiol Biomarkers Prey; 14: 2173-2177 (2005).
Cui, et al., "Detection of the human organic anion transporters SLC21A6 (OATP2) and SLC21A8 (OATP8) in liver and hepatocellular carcinoma." Lab Invest; 83: 527-538 (2003).
Cui, et al., "Hepatic uptake of bilirubin and its conjugates by the human organic anion transporter SLC21A6." J Biol Chem; 276: 9626-9630 (2001).
Dahut, et al., "Randomized phase II trial of docetaxel plus thalidomide in androgen-independent prostate cancer." J Clin Oncol; 22: 2532-2539 (2004).
Dawson, et al., "Phase II study of suramin plus aminoglutethimide in two cohorts of patients with androgen-independent prostate cancer: simultaneous antiandrogen withdrawal and prior antiandrogen withdrawal", Clin Cancer Res; 4: 37-44 (1998).
Dawson, et al., "Phase II trial of suramin, leuprolide, and flutamide in previously untreated metastatic prostate cancer". J Clin Oncol; 15: 1470-1477 (1997).
Figg, et al., "A randomized phase II trial of thalidomide, an angiogenesis inhibitor, in patients with androgen-independent prostate cancer." Clin Cancer Res; 7: 1888-1893 (2001).
Figg, et al., "A randomized, phase II trial of ketoconazole plus alendronate versus ketoconazole alone in patients with andorgen independent prostate cancer and bone metastases." J Urol; 173: 790-796 (2005).
Greenlee, et al., "Cancer Statistics, 2001". CA Cancer J. Clin. vol. 15, 15-36 (2001).
Gregory, et al., "Androgen receptor stabilization in recurrent prostate cancer is associated with hypersensitivity to low androgen." Cancer Res; 61: 2892-2898 (2001).
Gsur, et al., "Genetic polymorphisms and prostate cancer risk." World J Urol; 21: 414-423 (2004).
Haiman, et al., "The relationship between a polymorphism in CYP17 with plasma hormone levels and prostate cancer." Cancer Epidemiol Biomarkers Prey; 10: 743-748 (2001).
Imamoto, et al., "Pretreatment serum level of testosterone as a prognostic factor in Japanese men with hormonally treated stage D2 prostate cancer." Endocr J ; 48: 573-578 (2001).
Isern, et al., "Functional analysis and androgen-regulated expression of mouse organic anion transporting polypeptide 1 (Oatpl) in the kidney." Biochem Biophys Acta; 1518: 73-78 (2001).
Kakinuma, et al., "Serum sex steroid hormone levels and polymorphisms of CYP17 and SRD5A2: implication for prostate cancer risk." Prostate Cancer Prostatic Dis; 7: 333-337 (2004).

Keppler, et al., "The human hepatocyte-specific organic anion transporter encoded by the SLC21A8 gene." Gastroenterology; 122: 1545-1546; author reply 6 (2002).
Kerb, R. "Implications of genetic polymorphisms in drug transporters for pharmacotherapy." Cancer Lett; 234: 4-33 (2006).
Konig, et al., "A novel human organic anion transporting polypeptide localized to the basolateral hepatocyte membrane." Am J Physiol Gastrointest Liver Physiol; 278: G156-164 (2000).
Konig, et al., "Localization and genomic organization of a new hepatocellular organic anion transporting polypeptide," J Biol Chem; 275: 23161-23168 (2000).
Konig, et al., "Pharmacogenomics of human OATP transporters." Naunyn Schmiedebergs Arch Pharmacol; 372: 432-443 (2006).
Lu, et al., "Regulation of renal oatp mRNA expression by testosterone." Am J Physiol; 270: F332-337 (1996).
Mostaghel, et al., "The basic biochemistry and molecular events of hormone therapy." Cuff Urol Rep; 8: 224-232 (2007).
Ntais, et al., "Association of the CYP17 gene polymorphism with the risk of prostate cancer: a meta-analysis." Cancer Epidemiol Biomarkers Prey; 12: 120-126 (2003).
Pastinen, et al., "A system for specific, high-throughput genotyping by allele-specific primer extension on microarrays". Genome Research 10: 1031-1042 (2000).
Powell, et al., "CYP3A4 genetic variant and disease-free survival among white and black men after radical prostatectomy." J Urol; 172: 1848-1852 (2004).
Roche, et al., "A consensus DNA-binding site for the androgen receptor." Mol Endocrinol 6: 2229-2235 (1992).
Ross, et al., "Serum testosterone levels in healthy young black and white men." J Natl Cancer Inst; 76: 45-48 (1986).
Sakr, et al., "The frequency of carcinoma and intraepithelial neoplasia of the prostate in the young male patients", J. Urol., 150: 379, (1993).
Schafer, et al., "DNA variation and the future of human genetics". Nature Biotechnology 16: 33-39 (1998).
Scott, et al., "Carcinoma of the prostate in elderly men: indicence, growth characteristics and clinical significance", J. Urol., 101:602, (1969).
Sekine, et al., "Molecular physiology of renal organic anion transporters." Am J Physiol Renal Physiol; 290: F251-261 (2006).
Sharifi, et al., "A retrospective study of the time to clinical endpoints for advanced prostate cancer." BJU Int; 96: 985-989 (2005).
Sharifi, et al., "Androgen deprivation therapy for prostate cancer." Jama; 294: 238-244 (2005).
Soloway, et al., "Prognostic factors in patients with advanced prostate cancer." Urology; 33: 53-56 (1989).
Stanbrough, et al., "Increased expression of genes converting adrenal androgens to testosterone in androgen-independent prostate cancer." Cancer Res; 66: 2815-2825 (2006).
Titus, et al., "Testosterone and dihydrotestosterone tissue levels in recurrent prostate cancer." Clin Cancer Res; 11: 4653-4657 (2005).
Tsuchiya, et al., "Impact of IGF-I and CYP19 gene polymorphisms on the survival of patients with metastatic prostate cancer." J Clin Oncol; 24: 1982-1989 (2006).
Vatten, et al., "Androgens in serum and the risk of prostate cancer: a nested case-control study from the Janus serum bank in Norway." Cancer Epidemiol Biomarkers Prey; 6: 967-969 (1997).
Vesovic, et al., "Role of a CYP17 promoter polymorphism for familial prostate cancer risk in Germany." Anticancer Res; 25: 1303-1307 (2005).
Wang, et al., "Large-scale identification, mapping, and genotyping of single-nucleotide polymorphisms in the human genome". Science; 280:1077-1082 (1998).

* cited by examiner

Comparison of Survival Curves

Logrank Test
- Chi square: 6.789
- df: 1
- P value: 0.0092
- P value summary: **
- Are the survival curves sig different? Yes Median survival
- SLCO in Caucasian:T/T, T/G: 6.300
- SLCO in Caucasian:G/G: 8.500
  - Ratio: 0.7412
  - 95% CI of ratio: 0.04106 to 1.441

Hazard Ratio
- Ratio: 1.591
- 95% CI of ratio: 1.145 to 2.602

SLCO1B3 GENOTYPE

The present application is a National Phase Entry of PCT/US2008/086002 filed Jan. 8, 2008 which claims the benefit of U.S. Provisional Patent Application 60/879,503 filed Jan. 8, 2007, which are incorporated herein by reference in their entirety.

GOVERNMENT SUPPORT

This work described herein was supported by the National Institutes of Health. The U.S. Government may have certain rights in the invention.

The application includes a sequence listing as required under 37 C.F.R. §§ 1.821-1.825. The listing is incorporated herein by reference.

BACKGROUND

Steroid hormones have been implicated in playing a fundamental role in the pathogenesis of prostate cancer. Polymorphisms in the genes that code for enzymes or hormones involved in androgen regulatory pathway are proposed to influence an individual's risk for developing prostate cancer. Such polymorphic genes that exist within the androgen biosynthesis and/or metabolism pathway and which have been suggested to be associated with prostate cancer risk include 5α-reductase type 2 and the cytochrome P450 17α-hydroxylase (CYP17). CYP17 encodes an enzyme with both 17α-hydroxylase and 17,20-lyase activities, the rate-limiting steps in androgen biosynthesis.

The mechanisms involved in the transport of steroid hormones through biological membranes, and their accumulation within target cells, are still not completely understood. The lipophilic nature of steroid hormones has led to the concept that the cell membrane plays a passive role in the transport of steroids. However, several members of different uptake transporter families have been localized to this membrane domain. One large family of uptake transporters is the OATP (organic anion transporting polypeptides) family of solute carriers. Endogenous substances, such as bile acids, steroids, thyroid hormones, and prostaglandins are substrates of members of the OATP family. Encoding members of this family are expressed in human hepatocytes: SLCO1B1 encoding OATP1B1, SLCO1B3 encoding OATP1B3, and SLCO2B1 encoding OATP2B1. OATP1B3, located in the basolateral membrane of human hepatocytes, is involved in the hepatocellular uptake of endogenous and exogenous organic anions. Endogenous substrates for OATP1B3 include 17-glucuronosyl estradiol, dehydroepiandrosterone-3-sulfate (DHEAS), bile acids (e.g., cholyltaurine and cholylglycine), and peptide hormones (e.g., cholecystokinin-8 (CCK-8)). DHEAS affects the developing prostate cancer.

Since membrane transporters are modulators of steroid hormones absorption and tissue distribution, genetic polymorphisms in genes encoding these transporters may account for the risk of prostate cancer and the predicting of survival. While a polymorphism in SLCO1B3 has been associated with increased prostate cancer risk, the relationship of the SLCO1B3 polymorphism and clinical outcome remains unclear. Thus, there is a need in the art to assess polymorphism in SLCO1B3 and prostate cancer clinical outcome and for prostate cancer susceptibility.

SUMMARY

Provided herein are identifications of genes and sequence variances which can be useful in connection with predicting differences in response to treatment and selection of appropriate treatment of a disease or condition. Moreover, these gene and sequence variances can be useful in the diagnosis of cancer.

The polymorphism of SLCO1B3 may contribute to individual variability in the tissue distribution steroid hormones. Genetic variations in the SLCO1B3 gene were reported by Smith N F et al, 2007, who identified a 334T>G polymorphism in exon 3, which results in a serine to alanine change at amino acid 112 (Ser112Ala) of SLCO1B3. The functional consequence of this polymorphism showed differences in transport characteristics. Provided herein, for the first time are the functional consequences of SLCO1B3 polymorphisms in clinical outcome. Before now the relationship of the SLCO1B3 polymorphism and clinical outcome was unclear. Provided herein is an association between a SLCO1B3 polymorphism and survival in patients with androgen independent prostate cancer and methods of prognosis. Moreover, the invention described herein provides methods for determining if subjects are good candidates for androgen deprivation therapy, and for determining when subjects are likely to become unresponsive to androgen deprivation therapy.

This variance may be useful either during the drug development process or in guiding the optimal use of already approved compounds. DNA sequence variances in candidate genes (e.g., genes that may plausibly affect the action of a drug) are analyzed, leading to the establishment of diagnostic tests useful for improving the development of new pharmaceutical products and/or the more effective use of existing pharmaceutical products.

Also, described herein is the identification of gene sequence variances in SLCO1B3 that are predictive of prognosis of a subject.

Provided herein, according to one aspect, are methods of predicting prognostic outcome of subject suffering from androgen independent prostate cancer comprising determining a SLCO1B3 genotype status of a subject, and correlating the genotype status to the survival of the subject.

In one embodiment, the genotype status is determined by PCR methods, immunological methods, sequencing methods, RFLP, SNP Chip technology, expression level of SLCO1B3, or enzyme kinetics of SLCO1B3.

In one embodiment, PCR methods are one or more of real-time PCR, PCR, reverse transcriptase PCR, or allele-specific PCR.

In one embodiment, the SLCO1B3 genotype status at nucleotide position 334 is determined.

In one embodiment, the SLCO1B3 genotype status at nucleotide position 699 is determined.

In another embodiment, the SLCO1B3 genotype status at nucleotide positions 334 and 699 are determined.

In another embodiment, the SLCO1B3 genotype status of at amino acid position 112 is determined.

In one embodiment, the SLCO1B3 genotype status at amino acid position 112 is determined by one or more of immunological methods or sequencing methods.

In one embodiment, the homozygous variant comprises the GG genotype and homozygous wild-type comprises the TT genotype. However, the variant is actually more frequent, but the T allele is the reference (or wild-type) allele by convention.

In another embodiment, a homozygous wild-type genotype and a heterozygous genotype status correlates with lower median survival of androgen independent prostate cancer as compared to a homozygous variant genotype status.

In another embodiment, the homozygous wild-type and a heterozygous-type median survival comprises from between about 1.8 to about 10.8 years.

In another embodiment, the wild-type genotype status is one or more of S at amino acid position 112, T at nucleotide position 334, or G at nucleotide position 699. In one embodiment, wherein a homozygous variant SLCO1B3 genotype status correlates with increased median survival as compared to homozygous wild-type or a heterozygous genotype status of androgen independent prostate cancer.

In one embodiment, the variant SLCO1B3 genotype status is one or more of G at amino acid position 112, G at nucleotide position 334, or A at nucleotide position 699.

In another embodiment, a heterozygous genotype status correlates with increased intermediate median survival which is between a median survival of a homozygous wild-type and a homozygous variant genotype status.

In one embodiment, the methods further comprise administering a therapeutic amount of an anti-neoplastic agent to the subject.

In one embodiment, the anti-neoplastic agent comprises docetaxel.

In one embodiment, the methods further comprise co-administering one or more additional anti-neoplastic agents to the subject.

In one embodiment, the one or more additional anti-neoplastic agents are selected from cisplatin, cyclophosphamind, doxorubicin, prednisone, 5-FU, trastuzumab, 3G4, travacin, gemcitabine, estramustine, carboplatin, or radioimmunotherapy agents.

In one embodiment, the methods further comprise co-administering one or more additional therapeutic agents to the subject.

In one embodiment, the therapeutic agents are one or more of an immunomodulatory agent, anti-inflammatory agents, glucocorticoid, steroid, non-steriodal anti-inflammatory drug, leukotreine antagonist, β 2-agonist, anticholinergic agent, sulphasalazine, penicillamine, dapsone, antihistamines, anti-malarial agents, anti-viral agents, or antibiotics.

In one embodiment, the additional therapeutic agent is prednisone.

Provided herein, according to one aspect, are kits for the assessment of cancer treatment options, comprising oligonucleotide primes that amplify from about nucleotide 300 to about nucleotide 360 portion of SLCO1B3 and instructions for use.

Provided herein, according to one aspect, are kits for the assessment of cancer treatment options, comprising a microarray, at least one oligonucleotide primer that amplifies from about nucleotide 310 to about nucleotide 650 of SLCO1B3 and instructions for use.

Provided herein, according to one aspect, are methods for determining the therapeutic capacity of a treatment for androgen independent prostate cancer in a subject, comprising determining a SLCO1B3 genotype status of a subject or a cell of a subject; determining a pre-treatment tumor status in the subject; administering a therapeutically effective amount of a candidate agent to the subject; and determining a post-treatment tumor status in the subject.

In one embodiment, a modulation of tumor status indicates that the candidate agent is efficacious.

In one embodiment, the pre-treatment and post-treatment levels of tumor status are determined in a diseased tissue.

In one embodiment, the diseased tissue is one or more of a fetus, lung, heart, liver, breast, prostate, vasculature or nervous tissue.

Provided herein, according to one aspect, are methods for determining the therapeutic capacity of a candidate treatment for androgen independent prostate cancer, comprising providing a population of tumor cells with a known SLCO1B3 genotype status; contacting the cells with a candidate composition, and determining effect of the candidate composition on cell proliferation, wherein a decrease in cell proliferation indicates that the candidate composition may be efficacious.

In one embodiment, the methods further comprise correlating the effect with the genotype.

In one embodiment, the methods further comprise determining the SLCO1B3 genotype status of the tumor cells prior to or after providing the cells.

Provided herein, according to one aspect, are methods of treating a subject suffering from cancer, comprising determining a SLCO1B3 genotype status of a subject or a cell of a subject, and administering a therapeutic amount of a candidate agent to a variant or a wild-type subject.

In one embodiment, the genotype status is determined by PCR methods, immunological methods, sequencing methods, expression level of SLCO1B3, or enzyme kinetics of SLCO1B3.

In one embodiment, the subject is a mammal. In one embodiment, the mammal is a human.

In one embodiment, the candidate agent comprises docetaxel.

In one embodiment, the methods further comprise co-administering one or more additional therapeutic agents to variant or wild-type subject.

In one embodiment, the one or more additional therapeutic agents are selected from cisplatin, cyclophosphamind, doxorubicin, prednisone, 5-FU, trastuzumab, 3G4, travacin, gemcitabine, estramustine, carboplatin, prednisone, or radioimmunotherapy agents.

In one embodiment, the therapeutic agents are one or more of an immunomodulatory agent, anti-inflammatory agents, glucocorticoid, steroid, non-steriodal anti-inflammatory drug, leukotreine antagonist, β 2-agonist, anticholinergic agent, sulphasalazine, penicillamine, dapsone, antihistamines, anti-malarial agents, anti-viral agents, or antibiotics.

In one embodiment, the cancer is one or more of breast, prostate, lung, head and neck, mesothelioma, ovarian, urothelial, hepatocellular, bladder, esopheageal, or stomach.

In another embodiment, the invention provides methods of treating a subject having cancer by moldulating the activity or expression of OATP1B3 in a subject. In one embodiment, the subject is administered a OATP1B3 modulator.

Other embodiments of the invention are disclosed infra.

DETAILED DESCRIPTION

Figure 1:
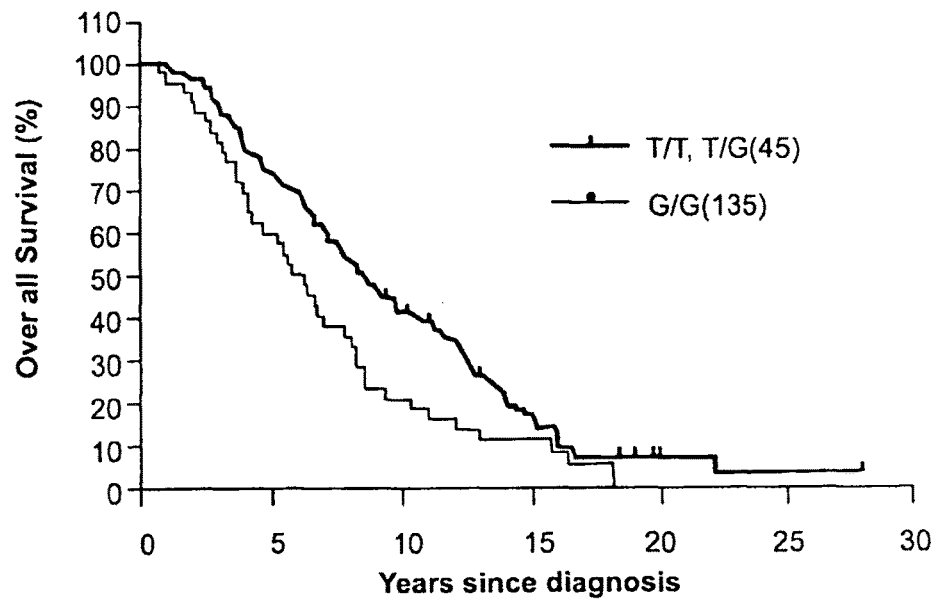
FIG. 1 depicts Kaplan-Meier over all survival curves in androgen independent prostate cancer patients of according to SLCO1B3-S112A (Nucleotide, 334T>G) genotypes (TT and TG vs GG).

Disclosed herein are methods of identifying and predicting inter-patient differences in prognostic prediction for survival in androgen independent prostate cancer. It further related to methods for determining and exploiting such differences to improve medical outcomes.

As used herein, the term "polymorphic site" refers to a region in a nucleic acid at which two or more alternative nucleotide sequences are observed in a significant number of nucleic acid samples from a population of subjects. A polymorphic site may be a nucleotide sequence of two or more nucleotides, an inserted nucleotide or nucleotide sequence, a deleted nucleotide or nucleotide sequence, or a microsatellite, for example. A polymorphic site may be two or more nucleotides in length, may be 3, 4, 5, 6, 7, 8, 9, 10, 11, 12, 13, 14, 15 or more, 20 or more, 30 or more, 50 or more, 75 or more, 100 or more, 500 or more, or about 1000 nucleotides in length, where all or some of the nucleotide sequences differ within the region. A polymorphic site is often one nucleotide in length, which is referred to herein as a single nucleotide polymorphism (SNP).

Where there are two, three, or four alternative nucleotide sequences at a polymorphic site, each nucleotide sequence is referred to as a "polymorphic variant" or "nucleic acid variant." Where two polymorphic variants exist, for example, the polymorphic variant represented in a minority of samples from a population is sometimes referred to as a "minor allele" and the polymorphic variant that is more prevalently represented is sometimes referred to as a "major allele." Many organisms possess a copy of each chromosome (e.g., humans), and those subjects who possess two major alleles or two minor alleles are often referred to as being "homozygous" with respect to the polymorphism, and those subjects who possess one major allele and one minor allele are normally referred to as being "heterozygous" with respect to the polymorphism. Individuals who are homozygous with respect to one allele are sometimes predisposed to a different phenotype as compared to subjects who are heterozygous or homozygous with respect to another allele.

The term "genotype" refers to the alleles present in DNA from a subject or patient, where an allele can be defined by the particular nucleotide(s) present in a nucleic acid sequence at a particular site(s). Often a genotype is the nucleotide(s) present at a single polymorphic site known to vary in the human population.

Furthermore, a genotype or polymorphic variant may be expressed in terms of a "haplotype," which as used herein refers to two or more polymorphic variants occurring within genomic DNA in a group of subjects within a population. For example, two SNPs may exist within a gene where each SNP position includes a cytosine variation and an adenine variation. Certain subjects in a population may carry one allele (heterozygous) or two alleles (homozygous) having the gene with a cytosine at each SNP position. As the two cytosines corresponding to each SNP in the gene travel together on one or both alleles in these subjects, the subjects can be characterized as having a cytosine/cytosine haplotype with respect to the two SNPs in the gene.

As used herein, the term "phenotype" refers to a trait which can be compared between subjects, such as presence or absence of a condition, a visually observable difference in appearance between subjects, metabolic variations, physiological variations, variations in the function of biological molecules, and the like. An example of a phenotype is length of survival. For example, a phenotype of a SLCO1B3 variant is longer survival of androgen independent prostate cancer, whereas a phenotype of a wild type subject is shorter survival of androgen independent prostate cancer.

The terms "variant form of a gene," "form of a gene," or "allele" refer to one specific form of a gene in a population, the specific form differing from other forms of the same gene in the sequence of at least one, and frequently more than one, variant sites within the sequence of the gene. The sequences at these variant sites that differ between different alleles of the gene are termed "gene sequence variances" or "variances" or "variants." The term "alternative form" refers to an allele that can be distinguished from other alleles by having distinct variances at least one, and frequently more than one, variant sites within the gene sequence. Other terms known in the art to be equivalent include mutation and polymorphism, although mutation is often used to refer to an allele associated with a deleterious phenotype. In the methods utilizing variance presence or absence, reference to the presence of a variance or variances means particular variances, e.g., particular nucleotides at particular polymorphic sites, rather than just the presence of any variance in the gene.

Variances occur in the human genome at approximately one in every 500-1,000 bases within the human genome when two alleles are compared. When multiple alleles from unrelated subjects are compared the density of variant sites increases as different subjects, when compared to a reference sequence, will often have sequence variances at different sites. At most variant sites there are only two alternative nucleotides involving the substitution of one base for another or the insertion/deletion of one or more nucleotides. Within a gene there may be several variant sites. Variant forms of the gene or alternative alleles can be distinguished by the presence of alternative variances at a single variant site, or a combination of several different variances at different sites (haplotypes).

The term "haplotype" refers to a cis arrangement of two or more polymorphic nucleotides, e.g., variances, on a particular chromosome, e.g., in a particular gene. The haplotype preserves information about the phase of the polymorphic nucleotides, that is, which set of variances were inherited from one parent, and which from the other. A genotyping test does not provide information about phase. For example, a subject heterozygous at nucleotide 25 of a gene (both A and C are present) and also at nucleotide 100 (both G and T are present) could have haplotypes 25A-100G and 25C-100T, or alternatively 25A-100T and 25C-100G. Phase can also be predicted statistically based on calculations of linkage frequencies, and the most likely phase can be assessed by such methods as well.

A polymorphic variant may be detected on either or both strands of a double-stranded nucleic acid. For example, a thymine at a particular position in a sequence can be reported as an adenine from the complementary strand. Also, a polymorphic variant may be located within an intron or exon of a gene or within a portion of a regulatory region such as a promoter, a 5' untranslated region (UTR), a 3' UTR, and in DNA (e.g., genomic DNA (gDNA) and complementary DNA (cDNA)), RNA (e.g., mRNA, tRNA, and rRNA), or a polypeptide. Polymorphic variations may or may not result in detectable differences in gene expression, polypeptide structure, or polypeptide function.

In one embodiment, SLCO1B3 334T>G is in linkage disequilibrium with 699G>A (Met233Ile). The 699G is linked to the 334T and the 699A is linked to the 334G.> Since we found that patient homozygous for the 334G SNP survive longest, it follows that patients "homozygous" for the 699A SNP also survive longest. It also follows that patients carrying at least one 699G polymorphism will be the same as those carrying at least one 334T polymorphism and will have shorter survival.

The terms "disease" or "condition" are commonly recognized in the art and designate the presence of signs and/or symptoms in a subject or patient that are generally recognized as abnormal. Diseases or conditions may be diagnosed and categorized based on pathological changes. Signs may include any-objective evidence of a disease such as changes that are evident by physical examination of a patient or the results of diagnostic tests that may include, among others, laboratory tests to determine the presence of DNA sequence variances or variant forms of certain genes in a patient. Symptoms are subjective evidence of disease or a patients condition, e.g., the patients perception of an abnormal condition that differs from normal function, sensation, or appearance, which may include, without limitations, physical disabilities, morbidity, pain, and other changes from the normal condition experienced by a subject. Various diseases or conditions include, for example, those categorized in standard textbooks of medicine including, without limitation, textbooks of nutrition, allopathic, homeopathic, and osteopathic medicine. In certain aspects, the disease or condition is selected from the group consisting of the types of diseases listed in standard texts such as Harrison's Principles of Internal Medicine (14th Ed) by Anthony S. Fauci, Eugene Braunwald, Kurt J. Isselbacher, et al. (Editors), McGraw Hill, 1997, or Robbins Pathologic Basis of Disease (6th edition) by Ramzi S. Cotran, Vinay Kumar, Tucker Collins & Stanley L. Robbins, W B Saunders Co., 1998, or the Diagnostic and Statistical Manual of Mental Disorders: DSM-IV (.sub.4th edition), American Psychiatric Press, 1994, or other texts described below.

The phrase "suffering from a disease or condition" means that a subject is either presently subject to the signs and symptoms, or is more likely to develop such signs and symptoms than a normal subject in the population. Thus, for example, a subject suffering from a condition can include a developing fetus, a subject to a treatment or environmental condition which enhances the likelihood of developing the signs or symptoms of a condition, or a subject who is being given or will be given a treatment which increase the likelihood of the subject developing a particular condition. Thus, methods of the present invention which relate to treatments of patients (e.g., methods for selecting a treatment, selecting a patient for a treatment, and methods of treating a disease or condition in a patient) can include primary treatments directed to a presently active disease or condition, secondary treatments which are intended to cause a biological effect relevant to a primary treatment, and prophylactic treatments intended to delay, reduce, or prevent the development of a disease or condition, as well as treatments intended to cause the development of a condition different from that which would have been likely to develop in the absence of the treatment.

The term "therapy" refers to a process that is intended to produce a beneficial change in the condition of a mammal, e.g., a human, often referred to as a patient. A beneficial change can, for example, include one or more of restoration of function, reduction of symptoms, limitation or retardation of progression of a disease, disorder, or condition or prevention, limitation or retardation of deterioration of a patient's condition, disease or disorder. Such therapy can involve, for example, nutritional modifications, administration of radiation, administration of a drug, behavioral modifications, and combinations of these, among others.

The terms "drug" and "therapeutic agent," as used herein refer to a chemical entity or biological product, or combination of chemical entities or biological products, administered to a subject to treat or prevent or control a disease or condition, e.g., an anti-neoplastic agent. The chemical entity or biological product is preferably, but not necessarily a low molecular weight compound, but may also be a larger compound, for example, an oligomer of nucleic acids, amino acids, or carbohydrates including without limitation proteins, oligonucleotides, ribozymes, DNAzymes, glycoproteins, lipoproteins, and modifications and combinations thereof. A biological product is preferably a monoclonal or polyclonal antibody or fragment thereof such as a variable chain fragment or single chain antibody, nanobody; cells; or an agent or product arising from recombinant technology, such as, without limitation, a recombinant protein, recombinant vaccine, or DNA construct developed for therapeutic, e.g., human therapeutic, use. The term "drug" may include, without limitation, compounds that are approved for sale as pharmaceutical products by government regulatory agencies (e.g., U.S. Food and Drug Administration (FDA), European Medicines Evaluation Agency (EMEA), and a world regulatory body governing the International Conference of Harmonization (ICH) rules and guidelines), compounds that do not require approval by government regulatory agencies, food additives or supplements including compounds commonly characterized as vitamins, natural products, and completely or incompletely characterized mixtures of chemical entities including natural compounds or purified or partially purified natural products. The term "drug" as used herein is synonymous with the terms "medicine," "pharmaceutical product," or "product." Most preferably the drug is approved by a government agency for treatment of a specific disease or condition. Included are "candidate compounds," which refers to a drug, agent or compound that is under investigation, either in laboratory or human clinical testing for a specific disease, disorder, or condition.

The term "probe," as used herein, refers to a molecule that detectably distinguishes between target molecules differing in structure. Detection can be accomplished in a variety of different ways depending on the type of probe used and the type of target molecule. Thus, for example, detection may be based on discrimination of activity levels of the target molecule, but preferably is based on detection of specific binding. Examples of such specific binding include antibody binding and nucleic acid probe hybridization. Thus, for example, probes can include enzyme substrates, antibodies and antibody fragments, and nucleic acid hybridization probes. Thus, in preferred embodiments, the detection of the presence or absence of the at least one variance involves contacting a nucleic acid sequence which includes a variance site with a probe, preferably a nucleic acid probe, where the probe preferentially hybridizes with a form of the nucleic acid sequence containing a complementary base at the variance site as compared to hybridization to a form of the nucleic acid sequence having a non-complementary base at the variance site, where the hybridization is carried out under selective hybridization conditions. Such a nucleic acid hybridization probe may span two or more variance sites. Unless otherwise specified, a nucleic acid probe can include one or more nucleic acid analogs, labels or other substituents or moieties so long as the base-pairing function is retained. For example, techniques such as OLA, TAQMAN, and methods described in US Patent Application Publication No. 2004/0121371, which is hereby incorporated by reference, are also useful detection methods according to the methods disclosed herein.

As used herein the term "chemical class" refers to a group of compounds that share a common chemical scaffold but which differ in respect to the substituent groups linked to the scaffold. Examples of chemical classes of drugs include, for example, phenothiazines, piperidines, benzodiazepines and aminoglycosides. Members of the phenothiazine class include, for example, compounds such as chlorpromazine hydrochloride, mesoridazine besylate, thioridazine hydrochloride, acetophenazine maleate trifluoperazine hydrochloride and others, all of which share a phenothiazine backbone. Members of the piperidine class include, for example, compounds such as meperidine, diphenoxylate and loperamide, as well as phenylpiperidines such as fentanyl, sufentanil and alfentanil, all of which share the piperidine backbone. Chemical classes and their members are recognized by those skilled in the art of medicinal chemistry. A preferred chemical class is that to which docetaxel belongs, e.g., the taxoid family. For example, see U.S. Pat. Nos. 4,814,470, 5,438,072, 5,698,582, and 5,714,512, which are hereby incorporated by reference in their entirety.

"Predicting prognostic outcome," refers to, for example, the determination or forecasting of length of survival and/or probability of survival. For example, this may be based on the genotype of a particular gene, for example, SLCO1B3.

"Genotype status," as used herein refers to the particular genotype of a subject, a tissue of a subject and/or of a cell of a subject. The genotype may be of just one gene, or may be of many genes. For example, the genotype status may be of SLCO1B3 and determined by detecting the presence or absence of a variation at nucleotide position 334 or amino acid position 112. The wild type genotype status of nucleotide position 334 is the "T allele" (TT and TG) and the variant is the "G allele" (GG). The wildtype genotype status of SLCO1B3 is S at amino acid 112, and the variant SLCO1B3 is amino acid A at 112. The genotype status may be determined, for example, by biochemical methods, e.g., array based methods, PCR based methods, and other method now known or later developed in the art.

"Anti-neoplastic agent," as used herein is an agent that will halt tumor growth, slow tumor growth, kill tumor cells, cause tumor cells to enter apoptosis, limit the blood supply to tumors and the like. Examples include, docetaxel, cisplatin, cyclophosphamind, doxorubicin, prednisone, 5-FU, trastuzumab (Herceptin™) 3G4 (travacin equivalent) travacin, gemcitabine, estramustine, carboplatin, radiation.

"Co-administering," as used herein refers to the administration with another agent, either at the same time, in the same composition, at alternating times, in separate compositions, or combinations thereof.

"One or more additional anti-neoplastic agents," refers to the selection of additional therapeutic agents that may be co-administered with the anti-neoplastic agent are selected from cisplatin, mitomycin, capecitabine, irinotecan, topotecan, estramustine, vinorelbine, cyclophosphamide, ifosfamide, doxorubicin, epirubicin, 5-FU, trastuzumab (Herceptin™), 3G4 (travacin equivalent) travacin, gemcitabine, estramustine, carboplatin, imatinib, gefitinib, erlotinib, cetuximab (Erbitux), bevacizumab (Avastin), thalidomide, or radiation.

As used herein, the terms "tumor" or "cancer" refer to a condition characterized by anomalous rapid proliferation of abnormal cells in one or both breasts of a subject. The abnormal cells often are referred to as "neoplastic cells," which are transformed cells that can form a solid tumor. The term "tumor" refers to an abnormal mass or population of cells (e.g., two or more cells) that result from excessive or abnormal cell division, whether malignant or benign, and pre-cancerous and cancerous cells. Malignant tumors are distinguished from benign growths or tumors in that, in addition to uncontrolled cellular proliferation, they can invade surrounding tissues and can metastasize. In breast cancer, neoplastic cells may be identified in one or both breasts only and not in another tissue or organ, in one or both breasts and one or more adjacent tissues or organs (e.g., lymph node), or in a breast and one or more non-adjacent tissues or organs to which the breast cancer cells have metastasized. As used herein, "tumor" or "cancer," refers to one or more of breast, prostate, lung, head and neck, mesothelioma, ovarian, urothelial, hepatocellular, bladder, esophageal, or stomach.

Prostate cancer, along with lung and colon cancer, are the three most common causes of death from cancer in men in the U.S., but prostate is by far the most prevalent of all human malignancies with the exception of skin cancer (Scott R. et al., J. Urol., 101:602, 1969; Sala W A et al., J. Urol., 150: 379, 1993). It is one of the top three causes of death from cancer in men in the United States (Greenlee R T et al., CA Cancer J. Clin. Vol 15, 2001). Currently, treatments available for prostate cancer require not only an early detection of the malignancy and a reliable assessment of the severity of the cancer or the prognosis of survival of androgen independent prostate cancer.

As used herein, "assessing the risk of cancer in a subject," refers to, for example, the determination of the clinical outcome based on percentages of, for example, survival given their genotype and treatment options.

"Providing," refers to obtaining, by for example, buying or making the, e.g., polypeptide, drug, polynucleotide, probe, and the like. The material provided may be made by any known or later developed biochemical or other technique. For example, polypeptides may be obtained from cultured cells. The cultured cells, for example, may comprise an expression construct comprising a nucleic acid segment encoding the polypeptide.

Cells and/or subjects may be treated and/or contacted with one or more anti-neoplastic treatments including, surgery, chemotherapy, radiotherapy, gene therapy, immune therapy or hormonal therapy, or other therapy recommended or proscribed by self or by a health care provider.

As used herein, "treating, preventing or alleviating cancer," refers to the prophylactic or therapeutic use of the therapeutic agents described herein.

"Substantially purified" when used in the context of a polypeptide or polynucleotide, or fragment or variant thereof that are at least 60% free, preferably 75% free and more preferably 90% free from other components with which they are naturally associated. An "isolated polypeptide" or "isolated polynucleotide" is, therefore, a substantially purified polypeptide or polynucleotide, respectively.

The term "subject" includes organisms which are capable of suffering from cancer or who could otherwise benefit from the administration of a compound or composition of the invention, such as human and non-human animals. Preferred human animals include human patients suffering from or prone to suffering from cancer or associated state, as described herein. The term "non-human animals" of the invention includes all vertebrates, e.g., mammals, e.g., rodents, e.g., mice, and non-mammals, such as non-human primates, e.g., sheep, dog, cow, chickens, amphibians, reptiles, etc.

A method for "predicting" or "diagnosing" as used herein refers to a clinical or other assessment of the condition of a subject based on observation, testing, or circumstances.

"Determining a level of expression" or "determining a genotype," may be by any now known or hereafter developed assay or method of determining expression level, for example, immunological techniques, PCR techniques, immunoassay, quantitative immunoassay, Western blot or ELISA, quantitative RT-PCR, and/or Northern blot. The level may be of RNA or protein, sequencing, real-time PCR, PCR, allele-specific PCR, Pyrosequencing, SNP Chip technology, or RFLP.

A sample or samples may be obtained from a subject, for example, by swabbing, biopsy, lavage or phlebotomy. Samples include tissue samples, blood, sputum, bronchial washings, biopsy aspirate, or ductal lavage.

"Therapeutically effective amount," as used herein refers to an amount of an agent which is effective, upon single or multiple dose administration to the cell or subject, in prolonging the survivability of the patient with such a disorder beyond that expected in the absence of such treatment.

Compositions described herein may be administered, for example, systemically, intratumorally, intravascularally, to a resected tumor bed, orally, or by inhalation.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (e.g., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. The primer must be sufficiently long to prime the synthesis of extension products in the presence of the inducing agent. The exact lengths of the primers will depend on many factors, including temperature, source of primer and the use of the method.

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res., 19:5081 (1991); Ohtsuka et al., J. Boil. Chem. 260:2605-2608 (1985); Rossolini et al., Mol. Cell Probes, 8:91-98 (1994)). The term nucleic acid is used interchangeably with gene, cDNA, mRNA, oligonucleotide, and polynucleotide.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

As used herein, the term "polymerase chain reaction" (PCR) refers to the methods of U.S. Pat. Nos. 4,683,195, 4,683,202, and 4,965,188, all of which are hereby incorporated by reference, directed to methods for increasing the concentration of a segment of a target sequence in a mixture of genomic DNA without cloning or purification. As used herein, the terms "PCR product" and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "recombinant DNA molecule" as used herein refers to a DNA molecule, which is comprised of segments of DNA joined together by means of molecular biological techniques.

As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

The terms "identical" or percent "identity," in the context of two or more nucleic acids or polypeptide sequences, refer to two or more sequences or subsequences that are the same or have a specified percentage of amino acid residues or nucleotides that are the same (e.g., 60% identity, optionally 65%, 70%, 75%, 80%, 85%, 90%, or 95% identity over a specified region), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Optionally, the identity exists over a region that is at least about 50 amino acids or nucleotides in length, or more preferably over a region that is 75-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math., 2:482 (1981), by the homology alignment algorithm of Needleman & Wunsch, J. Mol Biol., 48:443 (1970), by the search for similarity method of Pearson & Lipman, Proc. Natl. Acad. Sci. U.S.A., 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

The antibodies of the instant invention are raised against the different alleles of SLCO1B3, e.g., SLCO1B3 wild-type SLCO1B3 variant. The antibody can be a polyclonal, monoclonal, recombinant, e.g., a chimeric or humanized, fully human, non-human, e.g., murine, single chain antibody, or fully synthetic. Chimeric, humanized, but most preferably, completely human antibodies are desirable for applications which include repeated administration, e.g., therapeutic treatment of human patients, and some diagnostic applications. In a related embodiment, the antibody can be coupled to a toxin.

Methods of Detecting Cancer, Predicting Responsiveness, Selecting Subjects, and Assessing Risks of Treatments In one aspect, the invention provides a method for determining prognosis of a subject suffering from androgen independent prostate cancer by determining whether or not a gene or genes in cells of the patient (in some cases including both normal and disease cells, such as cancer cells) contain at least one sequence variance which is indicative of the survivability of the disease or condition. The methods disclosed herein may be used with other genotyping or tumor marker methods if necessary. Preferably the at least one variance includes a plurality of variances which may provide a haplotype or haplotypes. Preferably the joint presence of the plurality of variances is indicative of the survivability in a patient having such plurality of variances. The plurality of variances may also be combinations of these relationships. The plurality of variances may include variances from one, two, three or more gene loci.

In another aspect, methods of predicting prognosis of a subject comprise determining the genotype status of SLCO1B3, and correlating the genotype to the prognosis. The determining may comprise methods including, for example, array based methods, PCR based methods, immunological methods (antibodies, western blots, RIAs, etc), sequencing methods (direct and indirect sequencing of oligonucleotides or nucleic acids and peptides or proteins or Pyrosequencing), expression level of SLCO1B3 alleles, enzyme kinetics of SLCO1B3, PCR methods (real-time PCR, allele-specific PCR, reverse-transcriptase PCR, PCR), SNP Chip technology, RFLP and/or other assays described herein. The genotype status, refers to, for example, the genotype of one or both alleles of a humans SLCO1B3 gene. The genotype status of SLCO1B3 may comprise determining the identity of the nucleotide position 334 of SLCO1B3 and/or determining the identity of the amino acid position 112. The assay may be informative if only one allele is determined. For example, if only one allele is determined and it is wild-type, the assay is informative because both a heterozygous subject and a homozygous wild-type subject will be correlated with a shorter survivability. If only one allele is determined to be SLCO1B3 variant, correlates to a longer prognosis of survivability.

"Correlating," "correlation," "correlates," as used herein refer to the establishment of mutual or reciprocal relationship between genotype status and therapeutic efficacy of certain treatments as described herein. That is, correlating refers to relating the genotype status to risk, treatment.

As used herein, "homozygous variant SLCO1B3 genotype status," refers to the 112A variant of SLCO1B3 being found on both alleles of SLCO1B3. Subjects homozygous for the 334G survive longest (e.g., correlate with longer survival than 334T or increased median survival as compared to wild-type of androgen independent prostate cancer). Subjects heterozygous for 334G and 334T correlate with intermediate survival (e.g., survive an intermediate time between the homozygous 334T and 334G genotypes, increased intermediate median survival as compared to wild-type of androgen independent prostate cancer) and subjects homozygous for 334T correlate with the lowest survival (e.g., shorter survival than both the homozygous 334G and the heterozygous genotypes, decreased median survival as compared to wild-type of androgen independent prostate cancer). The SLCO1B3 T334G single nucleotide polymorphism is in linkage disequilibrium with 699G>A. The 699G is linked to the 334T and the 699A is linked to the 334G. Thus, the survival time correlate accordingly.

Subjects homozygous for the 699A survive longest (e.g., correlate with longer survival than 699G or increased median survival as compared to wild-type of androgen independent prostate cancer). Subjects heterozygous for 699A and 699G correlate with intermediate survival (e.g., survive an intermediate time between the homozygous 699A and 699G genotypes, increased median survival as compared to wild-type of androgen independent prostate cancer). Subjects homozygous for 699G correlate with the lowest survival (e.g., shorter survival than both the homozygous 699A and the heterozygous genotypes).

Methods described herein may further comprise administering a therapeutic amount of an anti-neoplastic agent to the subject.

As used herein, the terms "effective" and "effectiveness" includes both pharmacological effectiveness and physiological safety. Pharmacological effectiveness refers to the ability of the treatment to result in a desired biological effect in the patient. Physiological safety refers to the level of toxicity, or other adverse physiological effects at the cellular, organ and/or organism level (often referred to as side-effects) resulting from administration of the treatment. On the other hand, the term "ineffective" indicates that a treatment does not provide sufficient pharmacological effect to be therapeutically useful, even in the absence of deleterious effects, at least in the unstratified population. (Such a treatment may be ineffective in a subgroup that can be identified by the presence of one or more sequence variances or alleles.) "Less effective" means that the treatment results in a therapeutically significant lower level of pharmacological effectiveness and/or a therapeutically greater level of adverse physiological effects, e.g., greater liver toxicity.

Thus, in connection with the administration of a drug, a drug which is "effective against" a disease or condition indicates that administration in a clinically appropriate manner results in a beneficial effect for at least a statistically significant fraction of patients, such as a improvement of symptoms, a cure, a reduction in disease load, reduction in tumor mass or cell numbers, extension of life, improvement in quality of life, or other effect generally recognized as positive by medical doctors familiar with treating the particular type of disease or condition.

Effectiveness is measured in a particular population. In conventional drug development the population is generally every subject who meets the enrollment criteria (e.g., has the particular form of the disease or condition being treated).

The term "deleterious effects" refers to physical effects in a patient caused by administration of a treatment which are regarded as medically undesirable. Thus, for example, deleterious effects can include a wide spectrum of toxic effects injurious to health such as death of normally functioning cells when only death of diseased cells is desired, nausea, fever, inability to retain food, dehydration, damage to critical organs such as arrvhias, renal tubular necrosis, fatty liver, or pulmonary fibrosis leading to coronary, renal, hepatic, or pulmonary insufficiency among many others. In this regard, the term "adverse reactions" refers to those manifestations of clinical symptomology of pathological disorder or dysfunction is induced by administration or a drug, agent, or candidate therapeutic intervention. In this regard, the term "contraindicated" means that a treatment results in deleterious effects such that a prudent medical doctor treating such a patient would regard the treatment as unsuitable for administration. Major factors in such a determination can include, for example, availability and relative advantages of alternative treatments, consequences of non-treatment, and permanency of deleterious effects of the treatment.

In one embodiment, the correlation of patient responses to therapy according to patient genotype is carried out in a clinical trial, e.g., as described herein according to any of the variations described. Detailed description of methods for associating variances with clinical outcomes using clinical trials are provided below. Further, in preferred embodiments the correlation of pharmacological effect (positive or negative) to treatment response according to genotype or haplotype in such a clinical trial is part of a regulatory submission to a government agency leading to approval of the drug. Most preferably the compound or compounds would not be approvable in the absence of the genetic information allowing identification of an optimal responder population.

As indicated above, in aspects of this invention involving selection of a patient for a treatment, selection of a method or mode of administration of a treatment, and selection of a patient for a treatment or a method of treatment, the selection may be positive selection or negative selection. Thus, the methods can include eliminating a treatment for a patient, eliminating a method or mode of administration of a treatment to a patient, or elimination of a patient for a treatment or method of treatment.

The term "differential" or "differentially" generally refers to a statistically significant different level in the specified property or effect. Preferably, the difference is also functionally significant. Thus, "differential binding or hybridization" is a sufficient difference in binding or hybridization to allow discrimination using an appropriate detection technique. Likewise, "differential effect" or "differentially active" in connection with a therapeutic treatment or drug refers to a difference in the level of the effect or activity that is distinguishable using relevant parameters and techniques for measuring the effect or activity being considered. Preferably the difference in effect or activity is also sufficient to be clinically significant, such that a corresponding difference in the course of treatment or treatment outcome would be expected, at least on a statistical basis.

A "marker" refers to a protein or nucleic acid molecule that is correlated with a disease state or correlated with an increased or decreased risk of developing a disease state. In the instant application, exemplary markers are the SLCO1B3 with one or more of the single nucleotide polymorphisms described herein or OTAP1B3 having the corresponding amino acid sequence to SLCO1B3 with the single nucleotide polymorphisms described herein.

A "diagnostic amount" of a marker refers to an amount of a marker in a subject's sample that is consistent with a diagnosis of prostate cancer. A diagnostic amount can be either in absolute amount (e.g., µg/ml) or a relative amount (e.g., relative intensity of signals).

A "control amount" of a marker can be any amount or a range of amount, which is to be compared against a test amount of a marker. For example, a control amount of a marker can be the amount of a marker in a person without prostate cancer. A control amount can be either in absolute amount (e.g., µg/ml) or a relative amount (e.g., relative intensity of signals).

The invention provides methods for diagnosing prostate cancer in a subject. The presence of OATP1B3 in a prostate sample, e.g., a biopsy, is indicative of prostate cancer as normal cancer-free prostate expresses essentially no OATP1B3 (see Example 2 and FIG. 3).

First, the selected biomarkers, e.g., SLCO1B3 with one or more polymorphisms, are measured in a subject sample using the methods known in the art and described herein. Then, the measurements is compared with a diagnostic amount or control that distinguishes cancer from a non-cancer. The diagnostic amounts will reflect the information herein that the particular biomarkers are up-regulated or down-regulated in a cancer status compared with non-cancer. As is well understood in the art, the particular diagnostic amounts used can be adjusted to increase sensitivity or specificity of the diagnostic assay depending on the preference of the diagnostician. The test amounts as compared with the diagnostic amount thus indicates the presence of prostate cancer.

In some embodiments, the mere presence or absence of a marker detected with a detection cutoff, without quantifying the amount of marker, is useful and can be correlated with a probable diagnosis of prostate cancer. For example, OATP1B3 can be more frequently detected in human prostate cancer patients than in normal subjects. Thus, a detected presence of this marker in a subject being tested indicates that the subject has a higher probability of having prostate cancer.

In other embodiments, the measurement of markers can involve quantifying the markers to correlate the detection of markers with a probable diagnosis of prostate cancer. Thus, if the amount of the markers detected in a subject being tested is different compared to a control amount (i.e., higher than the control), then the subject being tested has a higher probability of having prostate cancer.

The correlation may take into account the amount of the marker or markers in the sample compared to a control amount of the marker or markers (up regulation of the marker) (e.g., in normal subjects in whom human cancer is undetectable). A control can be, e.g., the average or median amount of marker present in comparable samples of normal subjects in whom human cancer is undetectable. The control amount is measured under the same or substantially similar experimental conditions as in measuring the test amount. The correlation may take into account the presence or absence of the markers in a test sample and the frequency of detection of the same markers in a control.

In certain embodiments of the methods of detecting prostate cancer, the methods further comprise managing subject treatment based on the status. As aforesaid, such management describes the actions of the physician or clinician subsequent to detecting prostate cancer. For example, if the result of the methods of the present invention is inconclusive or there is reason that confirmation of status is necessary, the physician may order more tests. Alternatively, if the status indicates that surgery is appropriate, the physician may schedule the patient for surgery. In other instances, the patient may receive chemotherapy, radiation treatments, or chemical treatment, in lieu of, or in addition to, surgery.

The invention also provides for such methods where the markers are measured again after subject management. In these cases, the methods are used to monitor the status of the cancer, e.g., response to cancer treatment, remission of the disease or progression of the disease.

In another example, the methods for detecting markers can be used to assay for and to identify compounds that modulate expression of these markers in vivo or in vitro.

The methods of the present invention have other applications as well. For example, the markers can be used to screen for compounds that modulate the expression of the markers in vitro or in vivo, which compounds in turn may be useful in treating or preventing prostate cancer in patients. In another example, the markers can be used to monitor the response to treatments for prostate cancer.

Methods

Single nucleotide polymorphism (SNP) analysis may be done, for example, by parallel screening of SNPs on microarrays. Differential hybridization with allele-specific oligonucleotide (ASO) probes is most commonly used in the microarray format (Pastinen et al., Genome Research 2000). The requirement for sensitivity (e.g., low detection limits) has been greatly alleviated by the development of the polymerase chain reaction (PCR) and other amplification technologies that allow researchers to amplify exponentially a specific nucleic acid sequence before analysis (for a review, see Abramson et al., Current Opinion in Biotechnology, 4:41-47 (1993)). Multiplex PCR amplification of SNP loci with subsequent hybridization to oligonucleotide arrays has been shown to be an accurate and reliable method of simultaneously genotyping at least hundreds of SNPs; see Wang et al., Science, 280:1077 (1998); see also Schafer et al., Nature Biotechnology 16:33-39 (1998).

New experimental techniques for mismatch detection with standard probes, as defined in greater detail below, include, for example, OLA, RCA, Invader™, single base extension (SBE) methods, allelic PCR, and competitive probe analysis. In SBE assays, a polynucleotide probe is attached to a support and hybridized to target DNA. See also US Patent Application Publication No. 2004/0121371.

Generally, for SBE assays, probe sets are designed such that the nucleotide at the 3' end of the probe is either matched or mismatched with the queried base in the target. If the base matches and hybridizes, the DNA polymerase will extend the probe by one base in the presence of four labeled-terminator nucleotides. Alternately, if the 3' base is mismatched, the DNA polymerase does not extend the probe. Thus, the identity of the SNP or queried base in the target is determined by the probe set that is extended by the DNA polymerase.

Some probes form internal stem-loop structures resulting in target-independent self-extension of the probe thus giving a false positive signal that interferes with determination of the SNP base. The present invention aims to overcome such problems.

The polymerase chain reaction (PCR) is a widely known method for amplifying nucleic acids. Of the PCR techniques, RT-PCR (Reverse Transcription-PCR), competitive RT-PCR and the like are used for detecting and quantifying a trace amount of mRNA, and show their effectiveness.

In recent years, a real-time quantitative detection technique using PCR has been established (TaqMan PCR, Genome Res., 6 (10), 986 (1996), ABI PRISM™. Sequence Detection System, Applied Biosystems). This technique measures the amount of nucleic acids using a particular fluorescent-labeled probe (TaqMan probe). More specifically, this technique utilizes the following principles: For example, a fluorescent-labeled probe having a reporter dye at the 5' end and a quencher dye at the 3' end is annealed to the target DNA, and the DNA is subjected to normal PCR. As the extension reaction proceeds, the probe is hydrolyzed from the 5' end by the 5'-3' exonuclease activity possessed by DNA polymerase. As a result, the reporter dye at the 5' end is separated from the quencher dye at the 3' end, thereby eliminating the FRET (Fluorescence Resonance Energy Transfer, the reduction in fluorescence intensity owing to the decrease in the energy level of the reporter dye caused by the resonance of the two fluorescent dyes) effect produced by the spatial proximity between the two dyes, and increasing the fluorescence intensity of the reporter dye that has been controlled by the quencher dye. The target nucleic acid can be selectively quantified and detected in real-time by measuring the increase of the fluorescence intensity.

This technique is advantageous in that it can test various samples simultaneously in a short time, since, unlike the detection and quantification technique using conventional PCR it does not involve complicated steps, such as agarose gel electrophoresis of the amplified product after PCR and analysis of the electrophoresis pattern.

Generally, when conducting clinical tests in a clinical test center or the like, it is necessary to inspect an extremely large number of samples within a limited time. Therefore, there is considerable demand for the development of efficient test techniques. The real-time quantitative detection technique is a promising candidate to meet this demand.

The present inventors turned their attention to the real-time quantitative detection technique using PCR, and conceived that, if the detection technique can be utilized for detecting human P450 molecular species, the molecular species can be subjectively detected and quantified using the same apparatus under the same PCR conditions.

Determining the presence of a particular variance or plurality of variances in a particular gene in a patient can be performed in a variety of ways. In preferred embodiments, the detection of the presence or absence of at least one variance involves amplifying a segment of nucleic acid including at least one of the at least one variances. Preferably a segment of nucleic acid to be amplified is 500 nucleotides or less in length, more preferably 200 nucleotides or less, and most preferably 45 nucleotides or less. Also, preferably the amplified segment or segments includes a plurality of variances, or a plurality of segments of a gene or of a plurality of genes.

In another aspect determining the presence of a set of variances in a specific gene related to treatment of pharmacokinetic parameters associated efficacy or safety, e.g. drug-induced disease, disorder, dysfunction, or other toxicity-related gene or SLCO1B3 may entail a haplotyping test that requires allele specific amplification of a large DNA segment of no greater than 25,000 nucleotides, preferably no greater than 10,000 nucleotides and most preferably no greater than 5,000 nucleotides. Alternatively one allele may be enriched by methods other than amplification prior to determining genotypes at specific variant positions on the enriched allele as a way of determining haplotypes. Preferably the determination of the presence or absence of a haplotype involves determining the sequence of the variant site or sites by methods such as chain terminating DNA sequencing or minisequencing, or by oligonucleotide hybridization or by mass spectrometry.

In another aspect, the invention provides a method for determining a genotype of a subject in relation to one or more variances in one or more of the genes identified in above aspects by using mass spectrometric determination of a nucleic acid sequence which is a portion of a gene identified for other aspects of this invention or a complementary sequence. Such mass spectrometric methods are known to those skilled in the art. In preferred embodiments, the method involves determining the presence or absence of a variance in a gene; determining the nucleotide sequence of the nucleic acid sequence; the nucleotide sequence is 100 nucleotides or less in length, preferably 50 or less, more preferably 30 or less, and still more preferably 20 nucleotides or less. In general, such a nucleotide sequence includes at least one variance site, preferably a variance site that is informative with respect to the expected response of a patient to a treatment as described for above aspects.

In preferred embodiments, the detection of the presence or absence of the at least one variance involves contacting a nucleic acid sequence corresponding to one of the genes identified above or a product of such a gene with a probe. The probe is able to distinguish a particular form of the gene or gene product or the presence or a particular variance or variances, e.g., by differential binding or hybridization. Thus, exemplary probes include nucleic acid hybridization probes, peptide nucleic acid probes, nucleotide-containing probes which also contain at least one nucleotide analog, and antibodies, e.g., monoclonal antibodies, and other probes as discussed herein. Those skilled in the art are familiar with the preparation of probes with particular specificities. Those skilled in the art will recognize that a variety of variables can be adjusted to optimize the discrimination between two variant forms of a gene, including changes in salt concentration, temperature, pH and addition of various compounds that affect the differential affinity of GC vs. AT base pairs, such as tetramethyl ammonium chloride. (See Current Protocols in Molecular Biology by F. M. Ausubel, R. Brent, R. E. Kingston, D. D. Moore, J. D. Seidman, K. Struhl, and V. B. Chanda (editors), John Wiley & Sons).

In other preferred embodiments, determining the presence or absence of the at least one variance involves sequencing at least one nucleic acid sample. The sequencing involves sequencing of a portion or portions of a gene and/or portions of a plurality of genes that includes at least one variance site, and may include a plurality of such sites. Preferably, the portion is 500 nucleotides or less in length, more preferably 200 nucleotides or less, and most preferably 45 nucleotides or less in length. Such sequencing can be carried out by various methods recognized by those skilled in the art, including use of dideoxy termination methods (e.g., using dye-labeled dideoxy nucleotides) and the use of mass spectrometric methods. In addition, mass spectrometric methods may be used to determine the nucleotide present at a variance site. In preferred embodiments in which a plurality of variances is determined, the plurality of variances can constitute a haplotype or collection of haplotypes. Preferably the methods for determining genotypes or haplotypes are designed to be sensitive to all the common genotypes or haplotypes present in the population being studied (for example, a clinical trial population).

The process of genotyping involves using diagnostic tests for specific variances that have already been identified. It will be apparent that such diagnostic tests can only be performed after variances and variant forms of the gene have been identified. Identification of new variances can be accomplished by a variety of methods, alone or in combination, including, for example, DNA sequencing, SSCP, heteroduplex analysis, denaturing gradient gel electrophoresis (DGGE), heteroduplex cleavage (either enzymatic as with T4 Endonuclease 7, or chemical as with osmium tetroxide and hydroxylamine), computational methods (described in "VARIANCE SCANNING METHOD FOR IDENTIFYING GENE SEQUENCE VARIANCES" filed Oct. 14, 1999, Ser. No. 09/419,705, and other methods described herein as well as others known to those skilled in the art. (See, for example: Cotton, R. G. H., Slowly but surely towards better scanning for mutations, Trends in Genetics 13(2): 43-6, 1997 or Current Protocols in Human Genetics by N. C. Dracoli, J. L. Haines, B. R. Korf, D. T. Moir, C. C. Morton, C. E. Seidman, D. R. Smith, and A. Boyle (editors), John Wiley & Sons).

In the context of this invention, the term "analyzing a sequence" refers to determining at least some sequence information about the sequence, e.g., determining the nucleotides present at a particular site or sites in the sequence, particularly sites that are known to vary in a population, or determining the base sequence of all of a portion of the particular sequence.

Also usefully provided herein are probes which specifically recognize a nucleic acid sequence corresponding to a variance or variances in a gene as identified in aspects above or a product expressed from the gene, and are able to distinguish a variant form of the sequence or gene or gene product from one or more other variant forms of that sequence, gene, or gene product under selective conditions. Such genes, include, for example SLCO1B3, GenBank accession nos.: NM_019844; NM_001032941; AAH70264; NP_062818; EAW96415; EAW96414; EAW96413; Q9NPD5; and NP_001028113, which are hereby incorporated by reference in their entirety. Those skilled in the art recognize and understand the identification or determination of selective conditions for particular probes or types of probes. An exemplary type of probe is a nucleic acid hybridization probe, which will selectively bind under selective binding conditions to a nucleic acid sequence or a gene product corresponding to one of the genes identified for aspects above. Another type of probe is a peptide or protein, e.g., an antibody or antibody fragment which specifically or preferentially binds to a polypeptide expressed from a particular form of a gene as characterized by the presence or absence of at least one variance. Thus, in another aspect, the invention concerns such probes. In the context of this invention, a "probe" is a molecule, commonly a nucleic acid, though also potentially a protein, carbohydrate, polymer, or small molecule, that is capable of binding to one variance or variant form of the gene to a greater extent than to a form of the gene having a different base at one or more variance sites, such that the presence of the variance or variant form of the gene can be determined. Preferably the probe distinguishes at least one variance identified in Examples.

In one embodiment, the probe is a nucleic acid probe 6, 7, 8, 9, 10, 11, 12, 13, 14, or 15, preferably at least 17 nucleotides in length, more preferably at least 20 or 22 or 25, preferably 500 or fewer nucleotides in length, more preferably 200 or 100 or fewer, still more preferably 50 or fewer, and most preferably 30 or fewer. In preferred embodiments, the probe has a length in a range from any one of the above lengths to any other of the above lengths (including endpoints). The probe specifically hybridizes under selective hybridization conditions to a nucleic acid sequence corresponding to a portion of one of the genes identified in connection with above aspects. The nucleic acid sequence includes at least one and or more variant sites. Also in preferred embodiments, the probe has a detectable label, preferably a fluorescent label. A variety of other detectable labels are known to those skilled in the art. Such a nucleic acid probe can also include one or more nucleic acid analogs.

In connection with nucleic acid probe hybridization, the term "specifically hybridizes" indicates that the probe hybridizes to a sufficiently greater degree to the target sequence than to a sequence having a mismatched base at least one variance site to allow distinguishing such hybridization. The term "specifically hybridizes," thus refers to the probe hybridizing to the target sequence, and not to non-target sequences, at a level which allows ready identification of probe/target sequence hybridization under selective hybridization conditions. Thus, "selective hybridization conditions" refer to conditions that allow such differential binding. Similarly, the terms "specifically binds" and "selective binding conditions" refer to such differential binding of any type of probe, e.g., antibody probes, and to the conditions that allow such differential binding. Typically hybridization reactions to determine the status of variant sites in patient samples are carried out with two different probes, one specific for each of the (usually two) possible variant nucleotides. The complementary information derived from the two separate hybridization reactions is useful in corroborating the results. Likewise, provided herein are isolated, purified or enriched nucleic acid sequences of 15 to 500 nucleotides in length, preferably 15 to 100 nucleotides in length, more preferably 15 to 50 nucleotides in length, and most preferably 15 to 30 nucleotides in length, which has a sequence which corresponds to a portion of one of the genes identified for aspects above. Preferably the lower limit for the preceding ranges is 17, 20, 22, or 25 nucleotides in length. In other embodiments, the nucleic acid sequence is 30 to 300 nucleotides in length, or 45 to 200 nucleotides in length, or 45 to 100 nucleotides in length. The nucleic acid sequence includes at least one variance site. Such sequences can, for example, be amplification products of a sequence that spans or includes a variance site in a gene identified herein. Likewise, such a sequence can be a primer, or amplification oligonucleotide that is able to bind to or extend through a variance site in such a gene. Yet another example is a nucleic acid hybridization probe comprised of such a sequence. In such probes, primers, and amplification products, the nucleotide sequence can contain a sequence or site corresponding to a variance site or sites, for example, a variance site identified herein. Preferably the presence or absence of a particular variant form in the heterozygous or homozygous state is indicative of the longer survivability of a subject.

Likewise, the invention provides a set of primers or amplification oligonucleotides (e.g., 2, 3, 4, 6, 8, 10 or even more) adapted for binding to or extending through at least one gene identified herein.

In reference to nucleic acid sequences which "correspond" to a gene, the term "correspond" refers to a nucleotide sequence relationship, such that the nucleotide sequence has a nucleotide sequence which is the same as the reference gene or an indicated portion thereof, or has a nucleotide sequence which is exactly complementary in normal Watson-Crick base pairing, or is an RNA equivalent of such a sequence, e.g., an mRNA, or is a cDNA derived from an mRNA of the gene.

In the genetic analysis that associated cancer with the polymorphic variants described herein, samples from subjects having cancer and subjects not having cancer are genotyped. The term "genotyped" as used herein refers to a process for determining a genotype of one or more subjects, where a "genotype" is a representation of one or more polymorphic variants in a population. Genotypes may be expressed in terms of a "haplotype," which as used herein refers to two or more polymorphic variants occurring within genomic DNA in a group of subjects within a population. For example, two SNPs may exist within a gene where each SNP position includes a cytosine variation and an adenine variation. Certain subjects in a population may carry one allele (heterozygous) or two alleles (homozygous) having the gene with a cytosine at each SNP position.

The term "effective amount" refers to a dosage or amount that is sufficient to reduce, halt, or slow tumor progression to result in alleviation, lessening or amelioration of symptoms in a patient or to achieve a desired biological outcome, e.g., slow or stop tumor growth or reduction or disappearance of a tumor.

"Pharmaceutically acceptable excipients or vehicles" include, for example, water, saline, glycerol, ethanol, etc. Additionally, auxiliary substances, such as wetting or emulsifying agents, pH buffering substances, and the like, may be present in such vehicles.

In the therapeutic methods of the invention, a treatment compound can be administered to a subject in any of several ways. For example, an anticancer agent can be administered as a prophylactic to prevent the onset of or reduce the severity of a targeted condition. Alternatively, an anticancer agent can be administered during the course of a targeted condition.

In other therapeutic methods of the invention, provided are methods of treating a subject suffering from cancer, comprising determining a SLCO1B3 genotype status of a subject or a cell of a subject, and administering an anticancer agent to the subject. The genotype status may be determined as described herein.

A treatment compound can be administered to a subject, either alone or in combination with one or more therapeutic agents, as a pharmaceutical composition in mixture with conventional excipient, e.g., pharmaceutically acceptable organic or inorganic carrier substances suitable for parenteral, enteral or intranasal application which do not deleteriously react with the active compounds and are not deleterious to the recipient thereof. Suitable pharmaceutically acceptable carriers include for example, water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethylcellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds.

Such compositions may be prepared for use in parenteral administration, particularly in the form of liquid solutions or suspensions; for oral administration, particularly in the form of tablets or capsules; intranasally, particularly in the form of powders, nasal drops, or aerosols; vaginally; topically e.g. in the form of a cream; rectally e.g. as a suppository; etc. The agents or activators may also be administered via stent. Exemplary stents are described in US Patent Application Publication Nos: 20050177246; 20050171599, 20050171597, 20050171598, 20050169969, 20050165474, 20050163821, 20050165352, and 20050171593.

The pharmaceutical agents may be conveniently administered in unit dosage form and may be prepared by any of the methods well known in the pharmaceutical arts, e.g., as described in *Remington's Pharmaceutical Sciences* (Mack Pub. Co., Easton, Pa., 1980). Formulations for parenteral administration may contain as common excipients such as sterile water or saline, polyalkylene glycols such as polyethylene glycol, oils of vegetable origin, hydrogenated naphthalenes and the like. In particular, biocompatible, biodegradable lactide polymer, lactide/glycolide copolymer, or polyoxyethylene-polyoxypropylene copolymers may be useful excipients to control the release of certain agents.

Other potentially useful parenteral delivery systems include ethylene-vinyl acetate copolymer particles, osmotic pumps, implantable infusion systems, and liposomes. Formulations for inhalation administration contain as excipients, for example, lactose, or may be aqueous solutions containing, for example, polyoxyethylene-9-lauryl ether, glycocholate and deoxycholate, or oily solutions for administration in the form of nasal drops, or as a gel to be applied intranasally. Formulations for parenteral administration may also include glycocholate for buccal administration, methoxysalicylate for rectal administration, or citric acid for vaginal administration. Other delivery systems will administer the therapeutic agent(s) directly at a surgical site, e.g. after balloon angioplasty an agent may be administered by use of stents.

The concentration of one or more treatment compounds in a therapeutic composition will vary depending upon a number of factors, including the dosage of the agent to be administered, the chemical characteristics (e.g., hydrophobicity) of the composition employed, and the intended mode and route of administration. In general terms, one or more than one of the agents or activators may be provided in an aqueous physiological buffer solution containing about 0.1 to 10% w/v of a compound for parenteral administration.

It will be appreciated that the actual preferred amounts of active compounds used in a given therapy will vary according to e.g. the specific compound being utilized, the particular composition formulated, the mode of administration and characteristics of the subject, e.g. the species, sex, weight, general health and age of the subject. Optimal administration rates for a given protocol of administration can be readily ascertained by those skilled in the art using conventional dosage determination tests conducted with regard to the foregoing guidelines. Suitable dose ranges may include from about 1 µg/kg to about 100 mg/kg of body weight per day.

Therapeutic compounds of the invention are suitably administered in a protonated and water-soluble form, e.g., as a pharmaceutically acceptable salt, typically an acid addition salt such as an inorganic acid addition salt, e.g., a hydrochloride, sulfate, or phosphate salt, or as an organic acid addition salt such as an acetate, maleate, fumarate, tartrate, or citrate salt. Pharmaceutically acceptable salts of therapeutic compounds of the invention also can include metal salts, particularly alkali metal salts such as a sodium salt or potassium salt; alkaline earth metal salts such as a magnesium or calcium salt; ammonium salts such an ammonium or tetramethyl ammonium salt; or an amino acid addition salts such as a lysine, glycine, or phenylalanine salt.

The methods described herein and used to develop the methods here can utilize or utilized a variety of different informative comparisons to identify correlations. For example a plurality of pairwise comparisons of treatment response and the presence or absence of at least one variance can be performed for a plurality of patients. By "prediction of patient outcome" is meant to include, for example, a forecast of the patient's likely health status. This may include a prediction of the patient's response to therapy, rehabilitation time, recovery time, cure rate, rate of disease progression, predisposition for future disease, or risk of having relapse.

By "pathway" or "gene pathway" is meant the group of biologically relevant genes involved in a pharmacodynamic or pharmacokinetic mechanism of drug, agent, or candidate therapeutic intervention. These mechanisms may further include any physiologic effect the drug or candidate therapeutic intervention renders. Included in this are "biochemical pathways" which is used in its usual sense to refer to a series of related biochemical processes (and the corresponding genes and gene products) involved in carrying out a reaction or series of reactions. Generally in a cell, a pathway performs a significant process in the cell.

By "pharmacological activity" used herein is meant a biochemical or physiological effect of drugs, compounds, agents, or candidate therapeutic interventions upon administration and the mechanism of action of that effect.

The pharmacological activity is then determined by interactions of drugs, compounds, agents, or candidate therapeutic interventions, or their mechanism of action, on their target proteins or macromolecular components. By "agonist" or "mimetic" or "activators" is meant a drug, agent, or compound that activate physiologic components and mimic the effects of endogenous regulatory compounds. By "antagonists," "blockers" or "inhibitors" is meant drugs, agents, or compounds that bind to physiologic components and do not mimic endogenous regulatory compounds, or interfere with the action of endogenous regulatory compounds at physiologic components. These inhibitory compounds do not have intrinsic regulatory activity, but prevent the action of agonists. By "partial agonist" or "partial antagonist" is meant an agonist or antagonist, respectively, with limited or partial activity. By "negative agonist" or "inverse antagonists" is meant that a drug, compound, or agent that can interact with a physiologic target protein or macromolecular component and stabilizes the protein or component such that agonist-dependent conformational changes of the component do not occur and agonist mediated mechanism of physiological action is prevented. By "modulators" or "factors" is meant a drug, agent, or compound that interacts with a target protein or macromolecular component and modifies the physiological effect of an agonist. In one embodiment, the modulators of the invention are OATP1B3 modulators.

Pharmaceutical Compositions

The small molecule, peptide, nucleic acid, and antibody therapeutics described herein may be formulated into pharmaceutical compositions and be provided in kits. The pharmaceutical formulations may also be coated on medical devices or onto nano-particles for delivery.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, α-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical, transdermal, buccal, sublingual, intramuscular, intraperotineal, rectal, vaginal and/or parenteral administration. The formulations may conveniently be presented in unit dosage form and may be prepared by any methods well known in the art of pharmacy. The amount of active ingredient that can be combined with a carrier material to produce a single dosage form will generally be that amount of the compound that produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an antibody or complex of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluent commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert dilutents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

The preparations of the present invention may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

The compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound that is the lowest dose effective to produce a therapeutic effect. Such an effective dose will generally depend upon the factors described above. Generally, intravenous and subcutaneous doses of the compounds of this invention for a patient, when used for the indicated analgesic effects, will range from about 0.0001 to about 100 mg per kilogram of body weight per day, more preferably from about 0.01 to about 50 mg per kg per day, and still more preferably from about 1.0 to about 100 mg per kg per day. An effective amount is that amount that treats cancer or associated disease.

If desired, the effective daily dose of the active compound may be administered as one dose or as, two, three, four, five, six or more sub-doses administered separately at appropriate intervals throughout the day, optionally, in unit dosage forms.

While it is possible for a compound of the present invention to be administered alone, it is preferable to administer the compound as a pharmaceutical composition. Moreover, the pharmaceutical compositions described herein may be administered with one or more other active ingredients that would aid in treating a subject having a HIV infection. In a related embodiment, the pharmaceutical compositions of the invention may be formulated to contain one or more additional active ingredients that would aid in treating a subject having a HIV infection or associated disease or disorder.

The antibodies and complexes, produced as described above, can be provided in kits, with suitable instructions and other necessary reagents, in order to conduct immunoassays as described above. The kit can also contain, depending on the particular immunoassay used, suitable labels and other packaged reagents and materials (e.g., wash buffers and the like). Standard immunoassays, such as those described above, can be conducted using these kits. The pharmaceutical compositions can be included in a container, pack, kit or dispenser together with instructions, e.g., written instructions, for administration, particularly such instructions for use of the antibody or complex to treat or prevent cancer or associated disease. The container, pack, kit or dispenser may also contain, for example, one or more additional active ingredients that would aid in treating a subject having aberrant cell proliferation.

The therapeutic agents described herein are formulated into pharmaceutical preparations for administration.

Additional therapeutic agents may include, but are not limited to, immunomodulatory agents, anti-inflammatory agents (e.g., adrenocorticoids, corticosteroids (e.g., beclomethasone, budesonide, flunisolide, fluticasone, triamcinolone, methylprednisolone, prednisolone, prednisone, hydrocortisone), glucocorticoids, steroids, non-steriodal anti-inflammatory drugs (e.g., aspirin, ibuprofen, diclofenac, and COX-2 inhibitors), and leukotreine antagonists (e.g., montelukast, methyl xanthines, zafirlukast, and zileuton), beta2-agonists (e.g., albuterol, biterol, fenoterol, isoetharie, metaproterenol, pirbuterol, salbutamol, terbutalin formoterol, salmeterol, and salbutamol terbutaline), anticholinergic agents (e.g., ipratropium bromide and oxitropium bromide), sulphasalazine, penicillamine, dapsone, antihistamines, anti-malarial agents (e.g., hydroxychloroquine), antiviral agents, and antibiotics (e.g., dactinomycin (formerly actinomycin), bleomycin, erythomycin, penicillin, mithramycin, anthramycin (AMC))

Antibodies

Antibodies useful in the methods described herein are antibodies specific for and can distinguish alleles of SLCO1B3, for example, can distinguish between SLCO1B3 wild-type and SLCO1B3 variant. Methods of generating antibodies useful in the methods described herein are described more fully below.

Chimeric and humanized monoclonal antibodies, comprising both human and non-human portions, can be made using standard recombinant DNA techniques. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125, 023; Better et al. (1988) Science 240: 1041-1043; Liu et al. (1987) Proc. Natl. Acad. Sci. USA 84: 3439-3443; Liu et al. (1987) J. Immunol. 139: 3521-3526; Sun et al. (1987) Proc. Natl. Acad. Sci. USA 84: 214-218; Nishimura et al. (1987) Canc. Res. 47: 999-1005; Wood et al. (1985) Nature 314: 446-449; and Shaw et al. (1988) J. Natl. Cancer Inst. 80: 1553-1559); Morrison, S. L. (1985) Science 229: 1202-1207; Oi et al. (1986) BioTechniques 4: 214; Winter U.S. Pat. No. 5,225,539; Jones et al. (1986) Nature 321: 552-525; Verhoeyan et al. (1988) Science 239: 1534; and Beidler et al. (1988) J. Immunol. 141: 4053-4060.

Completely human antibodies are particularly desirable for therapeutic treatment of human patients. Such antibodies can be produced using transgenic mice that are incapable of expressing endogenous immunoglobulin heavy and light chains genes, but which can express human heavy and light chain genes. See, for example, Lonberg and Huszar (1995) Int. Rev. Immunol. 13: 65-93); and U.S. Pat. Nos. 5,625,126; 5,633,425; 5,569,825; 5,661,016; and 5,545,806. In addition, companies such as Abgenix, Inc. (Fremont, Calif.) and Medarex, Inc. (Princeton, N.J.), can be engaged to provide human antibodies directed against a selected antigen using technology similar to that described above.

Completely human antibodies that recognize a selected epitope can be generated using a technique referred to as "guided selection." In this approach a selected non-human monoclonal antibody, e.g., a murine antibody, is used to guide the selection of a completely human antibody recognizing the same epitope. This technology is described by Jespers et al. (1994) Bio/Technology 12: 899-903).

The term "monoclonal antibody" as used herein refers to an antibody obtained from a substantially homogeneous population of antibodies, e.g., the subject antibodies within the population are identical except for possible naturally occurring mutations that may be present in a small subset of the antibody molecules. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity (See, U.S. Pat. No. 4,816,567; and Morrison et al., Proc. Natl. Acad. Sci. USA 81: 6851-6855 (1984)).

The present monoclonal antibodies can be made using any procedure which produces monoclonal antibodies. For example, monoclonal antibodies of the invention can be prepared using hybridoma methods, such as those described by Kohler and Milstein, Nature, 256: 495 (1975). In a hybridoma method, a mouse or other appropriate host animal is typically immunized with an immunizing agent to elicit lymphocytes that produce antibodies that will specifically bind to the immunizing agent.

The monoclonal antibodies also can be made by recombinant DNA methods, such as those described in U.S. Pat. No. 4,816,567 (Cabilly et al.). DNA encoding the disclosed monoclonal antibodies can be readily isolated and sequenced using conventional procedures (e.g., by using oligonucleotide probes that are capable of binding specifically to genes encoding the heavy and light chains of antibodies). Libraries of antibodies or active antibody fragments also can be generated and screened using phage display techniques, e.g., as described in U.S. Pat. No. 5,804,440 to Burton et al. and U.S. Pat. No. 6,096,551 to Barbas et al.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in International Patent Application Publication No. WO 94/29348, published Dec. 22, 1994, and U.S. Pat. No. 4,342,566. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross-lining antigen.

As used herein, the term "antibody or fragments thereof" encompasses chimeric antibodies and hybrid antibodies, with dual or multiple antigen or epitope specificities, single chain antibodies and fragments, such as F(ab')2, Fab', Fab, scFv and the like, including hybrid fragments. Thus, fragments of the antibodies that retain the ability to bind their specific antigens are provided. For example, fragments of antibodies which maintain HIV gp120 binding activity are included within the meaning of the term "antibody or fragment thereof." Such antibodies and fragments can be made by techniques known in the art and can be screened for specificity and activity according to the methods set forth in the Examples and in general methods for producing antibodies and screening antibodies for specificity and activity (See Harlow and Lane. Antibodies, A Laboratory Manual. Cold Spring Harbor Publications, New York (1988)). Also included within the meaning of "antibody or fragments thereof" are conjugates of antibody fragments and antigen binding proteins (single chain antibodies) as described, for example, in U.S. Pat. No. 4,704,692, the contents of which are hereby incorporated by reference.

The fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase bio-longevity, to alter secretory characteristics; etc. In any case, the antibody or antibody fragment must possess a bioactive property, such as specific binding to its cognate antigen. Functional or active regions of the antibody or antibody fragment can be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment (Zoller, M. J. Curr. Opin. Biotechnol. 3: 348-354 (1992)).

Kits

In one aspect, kits for the assessment of prognosis are provided. The kits comprise oligonucleotide probes that differentiate the wild-type and variant alleles of SLCO1B3, wherein the allele nucleotide position 334 or the amino acid position 112. Optionally the kits contain instructions for use.

The oligonucleotide probes may be one or more of OLA, or Taqman.

The kits may comprise oligonucleotide primes that amplify from about nt 1 to about nt 450 portion of SLCO1B3 and instructions for use. The primers may be labeled.

In another aspect, kits for the assessment of cancer treatment options are provided and comprise an array and/or microarray, oligonucleotide primes that amplify from about nucleotide 300 to about nucleotide 360 portion of SLCO1B3 and instructions for use. Alternately or in addition, primers may be provided that amplify from about nucleotide 310 to about nucleotide 350 of SLCO1B3, from about nucleotide 320 to about nucleotide 345 of SLCO1B3, from about nucleotide 310 to about nucleotide 355 of SLCO1B3, from about nucleotide 315 to about nucleotide 350 of SLCO1B3, or other portion that one of skill in the art would determine necessary or adequate to amplify and detect the genotype status using array or microarray technology.

In another aspect, a kit for the assessment of cancer treatment options are provided and comprise antibodies that distinguish the wild type and variant (e.g., SLCO1B3) alleles. In another aspect, a kit for the diagnosis of prostate cancer is provided.

Optionally the kits may comprise instructions for use.

The kits described above may further contain enzymes, buffers, labeling agents, and/or pharmaceutical compositions for treatment.

In another aspect, the invention provides a kit containing at least one probe or at least one primer (or other amplification oligonucleotide) or both (e.g., as described above) corresponding to SLCO1B3 or other gene related to prognosis of a disease or condition, or other gene involved in absorption, distribution, metabolism, excretion, or in toxicity-related modification of a drug. The kits are preferably adapted and configured to be suitable for identification of the presence or absence of a particular variance or variances, which can include or consist of a nucleic acid sequence corresponding to a portion of a gene. A plurality of variances may comprise a haplotype of haplotypes. The kit may also contain a plurality of either or both of such probes and/or primers, e.g., 2, 3, 4, 5, 6, or more of such probes and/or primers. Preferably the plurality of probes and/or primers are adapted to provide detection of a plurality of different sequence variances in a gene or plurality of genes, e.g., in 2, 3, 4, 5, or more genes or to amplify and/or sequence a nucleic acid sequence including at least one variance site in a gene or genes.

Preferably one or more of the variance or variances to be detected are correlated with survivability of a subject suffering from androgen independent prostate cancer. In preferred embodiments, the kit contains components (e.g., probes and/or primers) adapted or useful for detection of a plurality of variances (which may be in one or more genes) indicative of the effectiveness of at least one treatment, preferably of a plurality of different treatments for a particular disease or condition. It may also be desirable to provide a kit containing components adapted or useful to allow detection of a plurality of variances indicative of the effectiveness of a treatment or treatment against a plurality of diseases. The kit may also optionally contain other components, preferably other components adapted for identifying the presence of a particular variance or variances. Such additional components can, for example, independently include a buffer or buffers, e.g., amplification buffers and hybridization buffers, which may be in liquid or dry form, a DNA polymerase, e.g., a polymerase suitable for carrying out PCR (e.g., a thermostable DNA polymerase), and deoxy nucleotide triphosphates (dNTPs). Preferably a probe includes a detectable label, e.g., a fluorescent label, enzyme label, light scattering label, or other label. Preferably the kit includes a nucleic acid or polypeptide array on a solid phase substrate. The array may, for example, include a plurality of different antibodies, and/or a plurality of different nucleic acid sequences. Sites in the array can allow capture and/or detection of nucleic acid sequences or gene products corresponding to different variances in one or more different genes. Preferably the array is arranged to provide variance detection for a plurality of variances in one or more genes which correlate with one or more of the prognosis of a subject or the effectiveness of one or more treatments of one or more diseases, one of which is a variance as described herein.

The kit may also optionally contain instructions for use, which can include a listing of the variances correlating with a prognosis predictor for survival in subjects with androgen independent disease, with particular treatment or treatments for a disease or diseases and/or a statement or listing of the diseases for which a particular variance or variances correlates with a treatment efficacy and/or safety.

Preferably the kit components are selected to allow detection of a variance described herein, and/or detection of a variance indicative of a treatment, e.g., prognostic predictor for survival in subjects with androgen independent prostate cancer, pointed out herein.

Additional configurations for kits of this invention will be apparent to those skilled in the art.

The invention also includes the use of such a kit to determine the genotype(s) of one or more subjects with respect to one or more variance sites in one or more genes identified herein. Such use can include providing a result or report indicating the presence and/or absence of one or more variant forms or a gene or genes which are indicative of the effectiveness of a treatment or treatments.

All documents mentioned herein are incorporated by reference herein in their entirety.

EXAMPLES

The present invention is further illustrated by the following non-limiting examples.

Example 1

Subjects

One hundred seventy nine white caucasian patients with androgen-independent prostate cancer were randomly selected from a biorepository consisting of patients, all of whom were maintained on androgen ablation therapy at the time of sample collection. All patients received standard definitive therapy, then appropriate hormonal ablation at the time of progression. All patients were enrolled in an IRB approved clinical trial within the intramural program of the National Cancer Institute and were arbitrarily assigned a number in our database. Informed consents were obtained from all subjects prior to trial participation. At the time of subject selection, we were blinded to all demographic information of the study subjects.

SLCO1B3 Genotype Analysis

Genomic DNA was extracted from serum or white blood cell buffy coat layers of whole blood using the either the QiAamp Ultrasens Viral DNA kit (serum) or the QIAamp DNA Blood Kit (buffy coat) as described by the manufacturer (Qiagen, Valencia, Calif.). Primer pairs were designed to amplify exon 3 of SLCO1B3 using a nested PCR protocol. The following primer set was used for primary PCR amplifications: forward, 5'-CCT TCA CAG TTA AAT TAC ATG GTC-3'(SEQ ID NO: 1) and reverse, 5'-TAT TCA TTT CAT ATA AAA CTG TAT ACC-3' (SEQ ID NO: 2). The DNA was amplified by 20 cycles of denaturation for 30 sec at 94° C., annealing for 30 sec at 62° C., and extension for 30 sec at 72° C. Secondary PCR amplifications were performed under the conditions of 40 cycles of denaturing for 30 sec at 94° C., annealing for 30 sec at 60° C., and extension for 30 sec at 72° C. using the following primer pairs: forward, 5'-GGG CAT ATT TGC ATT CAT TTG GG-3' (SEQ ID NO: 3) and reverse, 5'-CAT GAT AAA TAA AGA AAT ACA TGA TG-3' (SEQ ID NO: 4). The PCR was carried out in a 50-µl reaction mixture containing approximately 200 ng genomic DNA, PCR buffer, 1.5 mM MgCl2, 0.2 mM dNTPs, 0.8 pmol/µl of each primer, and 1.25 U Platinum Taq DNA polymerase (Invitrogen, Carlsbad, Calif.). All PCR amplifications were carried out using a DNA thermocycler (GeneAmp PCR system 9700, PE Applied Biosystems, Foster City, Calif.). After amplification, the quality of the amplified PCR products was verified by agarose gel electrophoresis.

DNA Sequence Analysis

Secondary PCR reaction products were directly sequenced in both directions using the following internal primer set: forward, 5'-CAC TAA GTC ATA TCA ACA TAA TTT TG-3' (SEQ ID NO: 5) or reverse, 5'-GCA TAC CTA TAG GTA TTC CTC TC-3' (SEQ ID NO: 6). Sequence analyses were carried out using Big Dye Terminator Cycle Sequencing Kit on an ABI PRISM 310 Genetic Analyzer (Applied Biosystems, Foster City, Calif.).

Statistical Analysis

Genotyping data was categorized into TT, TG, and GG. Associations between SLCO1B3 genetic variation and patient characteristics were evaluated by the exact Kruskal-Wallis. Patients who died were assessed as complete, whereas those who remained alive were censored at the date of last follow-up. The probability of survival as a function of time was determined by the Kaplan-Meier method. The statistical significance of the differences in median survival among the genotypes was determined by the log-rank test.

179 patients with androgen independent prostate cancer were analyzed for the presence of the −334T>G variant of SLCO1B3 (SLCO1B3-S112A). Characteristics (age of diagnosis, Gleason score) of the study subjects are presented in Table I. The median age of diagnosis was 61 years for patients. The frequencies of the incidence of the SLCO1B3-S112A polymorphism are shown in Table II. The SLCO1B3-S112A genotype distribution was 7.3% TT (13/179), 17.9% TG (32/179), and 74.9% GG (134/179). The T allele and G allele frequency of SLCO1B3-S112A was 0.16 and 0.84, respectively. Analyses of the association of the SLCO1B3-S112A genotypes with age at diagnosis and Gleason score in patients were also evaluated. Gleason scores were categorized as mildly aggressive (<7), moderately aggressive (7) or highly aggressive (8-10). No significant differences were observed in the frequencies of the SLCO1B3-S112A genotypes in relation to categorized Gleason scores (p=0.954) or age at diagnosis (p=0.984) as shown in Table III.

It was next determined whether the SLCO1B3-S112A polymorphism was associated with overall patient survival. The duration of survival was computed from the date of prostate cancer diagnosis until the date of death or last follow-up. One hundred sixty one (161) of the 179 patients had expired prior to analysis. The probability of survival over time was determined by the kaplan-meier method according to the genotype expressions (TT+TG vs. GG) as shown in FIG. 1. The statistically significant difference in overall survival between the two groups was observed (p=0.0105, by logrank test). However, this analysis includes deaths 15-25 years after diagnosis, when other causes of death may have reduced the difference between the groups' survival rate. In the intermediate range of follow-up, the estimated median survival time of the 179 patients with androgen independent prostate cancer was 7.8 years, but the median survival for the 45 patients with the tt or tg genotype was 6.3 years compared to 8.4 years for the combined 134 patients with either the GG genotype. Similarly, the survival probability at 10 years (20.1% in TT+TG vs 41.1% in GG genotype) is observed. The results suggest that patient survival was significantly prolonged for those with the variant g allele as compared to T allele group.

Androgens play an essential role in regulating the growth of prostate cancer cells and are therefore important in the etiology of prostate cancer. Changes in the expression of genes within the steroid hormone transport pathway may affect hormone distribution. The present study examines one such gene by assessing the disposition of a SLCO1B3-S112A polymorphism to predicting prostate cancer overall survival. The effect of polymorphic T to G transition in the SLCO1B3 remains unclear, which may cause a higher or lower transport activity measured for the G allelic variant as compared to that of its wild-type (T allele).

There have been no reports of the association between the SLCO1B3-S112A polymorphism and prostate cancer risk or clinical outcome. There has been no epidemiological study evaluating the incidence of SLCO1B3-S112A polymorphism to overall survival in patients with androgen independent prostate cancer. This is the first report demonstrating a statistically significant association of the SLCO1B3-S112A allelic variant with survival for an androgen independent patient population. Patients with the G allele genotype had a significantly longer survival advantage as compared with patients expressing the T allele. The −334T>G substitution (G allele) affect transport activity of some steroid such as 17-beta-glucuronosyl estradiol, cholyltaurine, dehydroepiandrosterone-3-sulfate, estrone-3-sulfate.

TABLE 1

Patient's characteristics

| | |
|---|---|
| No. of patients | 179 |
| Age at Diagnosis | |
| <49 | 18 |
| 50-59 | 57 |
| 60-69 | 78 |
| >70 | 26 |
| Gleason score | |
| 2-6 | 24 |
| 7 | 49 |
| 8-10 | 92 |
| unknown | 14 |

TABLE 2

Distribution of SLCO1B3-S112A polymorphism to race for androgen independent prostate cancer patients and healthy volunteers

| S112A | Present study | Caucasian[1] | African American[1] | Japanese[2] |
|---|---|---|---|---|
| TT | 13 (7.3%) | 0 (0) | 34 (37.8%) | 7 (8.9%) |
| TG | 32 (17.9%) | 23 (24.5%) | 38 (42.2%) | 29 (36.7%) |
| GG | 134 (74.9%) | 71 (75.5%) | 18 (20%) | 43 (54.4%) |

Data represented as number of patients (Present study) and healthy volunteers (Caucasian, African American, and Japanese), with percentage in parenthesis.
[1]Reference by Smith N et al. Clin Pharmacol Ther, 81: 76-82(2007)
[2]Reference by Tsujimoto M et al. Drug Metab Pharmacokinet, 21: 165-169 (2006)

TABLE 3

Associations between SLCO1B3-S112A genotype and Patient's characteristics with prostate cancer

| | TT | TG | GG | P |
|---|---|---|---|---|
| Age at Diagnosis | | | | 0.984 |
| <49 | 0 | 4 | 14 | |
| 50-59 | 4 | 10 | 43 | |
| 60-69 | 7 | 13 | 58 | |
| >70 | 2 | 5 | 19 | |
| Gleason score | | | | 0.954 |
| 2-6 | 1 | 4 | 19 | |
| 7 | 5 | 6 | 38 | |
| 8-10 | 6 | 19 | 67 | |
| unknown | 1 | 3 | 10 | |

Genotyping data was categorized into TT, TG, and GG.
Associations between SLCO1B3 genetic variation and patient characteristics were evaluated by the exact Kruskal-Wallis test.

A number of embodiments of the invention have been described.

Nevertheless, it will be understood that various modifications may be made without departing from the spirit and scope of the invention. Accordingly, other embodiments are within the scope of the following claims.

Example 2: Characterization of SLCO1B3 in Subjects Having Cancer

This Example examined: 1) the SLCO1B3 genotype in cancer cells as well as the uptake of testosterone by cells transfected with genetic variants of SLCO1B3; 2) the expression of OATP1B3 in normal prostate, benign prostatic hyperplasia and prostatic cancer, and 3) the role of SCLO1B3 haplotype on clinical outcome of Caucasian patients with androgen-independent prostatic cancer.

Materials and Methods

Genotyping of SLCO1B3 in Cancer Cell Lines

The analysis of SLCO1B3 genotype was performed on the NCI-60 panel of tumor cell lines (Developmental Therapeutics Program, NCI, www.dtp.nci.nih.gov). Genomic DNA was extracted from cells using either the QiAamp Ultrasens Viral DNA or QIAamp DNA Blood kits (Qiagen, Valencia, Calif.). Primer pairs (Table 4) were designed on the basis of the SLCO1B3 gene sequence available at GenBank (accession number NM_019844.1). PCR reactions were carried out in a 50-µl reaction mixture containing 200 ng of genomic DNA, 1×PCR buffer (Invitrogen, Carlsbad, Calif.), 1.5 mM $MgCl_2$, 0.2 mM dNTPs, 0.8 pmol/µl of each primer, and 1.25 U Platinum Taq DNA polymerase (Invitrogen, Carlsbad, Calif.). PCR amplifications were carried out using the GeneAmp PCR system 9700 (PE Applied Biosystems, Foster City, Calif.) with the following thermal profile (primary PCR): 20 cycles of denaturation at 94° C. for 30 sec, annealing at 62° C. for 30 sec, and extension at 72° C. for 30 sec. Secondary PCR amplifications were performed by 40 cycles at the same thermal profile with the exception of the annealing temperature that was 60° C. After amplification, the quality of the amplified PCR products was verified by agarose gel electrophoresis.

Secondary PCR reaction products were sequenced in both directions using the internal primer set reported in Table 4. Sequence analyses were carried out using the Big Dye Terminator Cycle Sequencing Kit on an ABI PRISM 3130 Genetic Analyzer. (Applied Biosystems, Foster City, Calif.). SLCO1B3 genotypes were compared to mRNA levels analyzed by an Affymetrix microarray platform (see http://dtp.nci.nih.gov/mtweb, Pattern Id: GC91812 by Developmental Therapeutics Program, NCI, NIH).

Cell Transfection and Transport Assay of Testosterone

Cos-7 cells (American Type Culture Collection, Manassas, Va.) were cultured in DMEM (GIBCO, Carlsbad, Calif.) with 10% FBS in an atmosphere of 5% $CO_2$-95% air at 37.degree. C. Cells were transfected with the pCMV6-XL4 DNA vector containing WT SLCO1B3 (TG), single (GG, TA) or double (GA) variants. The plasmid containing the polymorphisms was obtained by site-directed mutagenesis and transiently transfected by Lipofectamine (Invitrogen, Carlsbad, Calif.). The human SLCO1B3 cDNA cloned into the pCMV6-XL4 plasmid vector was purchased from OriGene Technologies (Rockville, Mo.). Nucleotide exchange was introduced into the cDNA of SLCO1B3 using the QuikChange Site-Directed Mutagenesis Kit (Stratagene, La Jolla, Calif.). The primer pairs used for the exchange of 334T>G and 699G>A are reported in Table 4. Successful mutagenesis was verified by sequencing.

TABLE 4

Primer sequences for PCR, sequencing and site-directed mutagenesis

| SNP | Use | | Primer sequence |
|---|---|---|---|
| 334T > G | PCR-I | (F) | CCTTCACAGTTAAATTACATGGTC |
| | PCR-I | (R) | TATTCATTTCATATAAAACTGTATACC |
| | PCR-II | (F) | GGGCATATTTGCATTCATTTGGG |
| | PCR-II | (R) | CATGATAAATAAAGAAATACATGATG |
| | Seq | (F) | CACTAAGTCATATCAACATAATTTTG |
| | Seq | (R) | GCATACCTATAGGTATTCCTCTC |
| | Mut | (F) | TGGGAACTGGAAGTATTTTGACATCTTTACCACATTTCTTCATG |
| | Mut | (R) | CATGAAGAAATGTGGTAAAGATGTCAAAATACTTCCAGTTCCCA |
| 699G > A | PCR-I | (F) | TCCTTGTATTTAGGTAACGTACAG |
| | PCR-I | (R) | TCAAGTTTGGTTATTTTGGATCAAG |
| | PCR-II | (F) | GATCTACCCTTGAAATAATAATGTC |
| | PCR-II | (R) | GTAAAAGCAAAGTATAAATAGGAGC |
| | Seq | (F) | TAAAAGCATGTTAAATGAAAACCAAG |
| | Seq | (R) | AAATAGTAAACAAAGAACTATTGAAAG |
| | Mut | (F) | GGGATCTCTGTTTGCTAAAATGTACGTGGATATTGGATATGTAG |
| | Mut | (R) | CTACATATCCAATATCCACGTACATTTTAGCAAACAGAGATCCC |
| 1564G > T | PCR-I | (F) | ATATACAGAATTTCATACACTAATTTC |
| | PCR-I | (R) | AATTCTAAGAAAATGCATTCTCAAAG |
| | PCR-II | (F) | TATTTTGCCTTCACTATTAAGCAA |
| | PCR-II | (R) | AATATGAATTTGAGCTCAAAATACAG |
| | Seq | (F) | GGAATGTATTCATAGCCCTGTTG |
| | Seq | (R) | ATGACAATGTTTTACAGGATCATA |

F, forward; R, reverse; PCR-I, primary PCR; PCR-II, secondary PCR; Seq, sequencing; Mut, site-directed mutagenesis Cellular uptake of testosterone was measured in SLCO1B3-transfected Cos-7 cells incubated in DMEM with 10% FBS containing 20 nM [$^3$H]-testosterone (76 Ci/mmol; Sigma-Aldrich) for 1 hour. The monolayers were rapidly washed thrice with buffer (142 mM NaCl, 5 mM KCl, 1 mM $K_2HPO_4$, 1.2 mM $MgCl_2$, 5 mM D-glucose, and 12.5 mM HEPES, pH 7.2, at 4° C.), solublized in 0.5 ml of 1 N NaOH, and the amount of radioactivity was measured by the LS 6000IC scintillation counter (Beckman Coulter, Fullerton, Calif.).

Analysis of OATP1B3 in Prostate Tissue by Immunofluorescence Microscopy

MaxArray™ Prostate Cancer & BPH Tissue Microarray Slides (Zymed Labs, San Francisco, Calif.) were used to assess OATP1B3 expression by immunofluorescence. The slide arrays, which contain tissue specimens from prostate cancer (20 cases), benign prostate hyperplasia (BPH, 19 cases), and one normal control, were deparaffinized and rehydrated, and then blocked and incubated with goat polyclonal OATP1B3 primary antibody (Santa Cruz Biotech, Santa Cruz, Calif.) at a final concentration of 20 µg/mL overnight at 4° C. Arrays were incubated with the secondary Alexa Fluor® 568 labeled donkey anti-goat IgG (Invitrogen, Carlsbad, Calif.) at 10 µg/mL, for 30 min at 25° C. Immunofluorescence microscopy was performed on Zeiss Axio Imager A1 (Carl Zeiss, Jena, Germany).

Study Population and Genotyping

Genomic DNA and clinical history was available from 180 Caucasian patients with androgen-independent prostate cancer enrolled in 1RB approved trials, including ketoconazole-alendronate, (21) suramin, (22-24) thalidomide-docetaxel, (25) thalidomide, (26) and sorafenib (protocol identifier at ClinicalTrials.gov: NCT00093431, last accessed on Aug. 13, 2007), within the intramural program of the NCI/NIH. Details of study population are given in Table 5. Prior to enrollment, patients were treated with androgen deprivation therapy consisting of either surgical castration, or luteinizing hormone-releasing hormone (LHRH) agonist with or without non-steroidal anti-androgens as the initial hormone therapy. DNA was also obtained from 131 healthy Caucasian individuals (median age=37 years). Informed consents were obtained from all subjects prior to trial participation. DNA was extracted from serum or white blood cell buffy coat layers; sequencing was performed as described above for cell lines to stratify patients on the basis of the SLCO1B3 TT/GG (WT), TG/GA and GG/AA haplotypes.

TABLE 5

Demographic and clinical characteristics of patients

| | |
|---|---|
| Total | 180 |
| Age at Diagnosis | |
| <49 | 19 |
| 50-59 | 57 |
| 60-69 | 78 |
| >70 | 26 |
| Gleason score | |
| 4-6 | 24 |
| 7 | 49 |
| 8-10 | 93 |
| unknown | 14 |
| Clinical Stage | |
| B | 48 |
| C | 45 |
| D1 | 14 |
| D2 | 70 |
| D3 | 1 |
| Unknown | 2 |
| Hormone therapy | |
| Surgical castration | 4 |
| LHRH analogues (leuprolide, goserelin) | 9 |
| CAB | 167 |
| Clinical study treatment | |
| Ketoconazole/alendronate | 47 |
| Suramin | 45 |
| Thalidomide/docetaxel | 40 |
| Thalidomide | 36 |
| Others | 12 |

CAB: combined androgen blockade (LHRH analogue plus androgen receptor antagonist)

Statistical Analysis

The comparison of testosterone uptake between cells transfected with WT and genetic variants of SLCO1B3 was performed by Tukey's multiple comparison test. Association between the SLCO1B3 genotypes and clinical outcome was evaluated by the exact Kruskal-Wallis test. Patients who had deceased were assessed as complete, whereas those who remained alive were censored at the date of last follow-up. The probability of survival as a function of time was determined by the Kaplan-Meier method. The statistical significance of the differences in overall survival and survival probability were determined by the log-rank and permutation tests. (27) A power analysis was not conducted due to the pilot nature of this study, and all samples available to us were genotyped.

Experimental Design

SLCO1B3 genotype was assessed in the NCI-60 panel of tumor cells by sequencing, while testosterone transport was analyzed in Cos-7 cells transfected with wild-type (WT), 334G and 699A SLCO1B3 variants. OATP1B3 expression in prostatic tissues was examined by fluorescence microscopy and the relationship between SLCO1B3 haplotypes and survival was examined in patients.

Results

Frequency Distribution of SLCO1B3 Genotype in NCI-60 Cell Lines

The uncommon 1564T variant was not detected in cell lines. The 334T>G and 699G>A SNPs were in complete linkage disequilibrium, with the exception of RXF393 renal tumor cells carrying the TT/GA haplotype. The majority of cell lines displayed the variant haplotype (GG/AA, n=49), the remaining the WT (TT/GG, n=3) and the heterozygous TG/GA (n=6) haplotypes. The genotype and the expression levels of SLCO1B3 were unrelated, as no specific genotype was associated with high or low expression of SLCO1B3 (data not shown).

In Vitro Uptake of Testosterone by SLCO1B3 Transfected Cos-7 Cells

Figure 2:
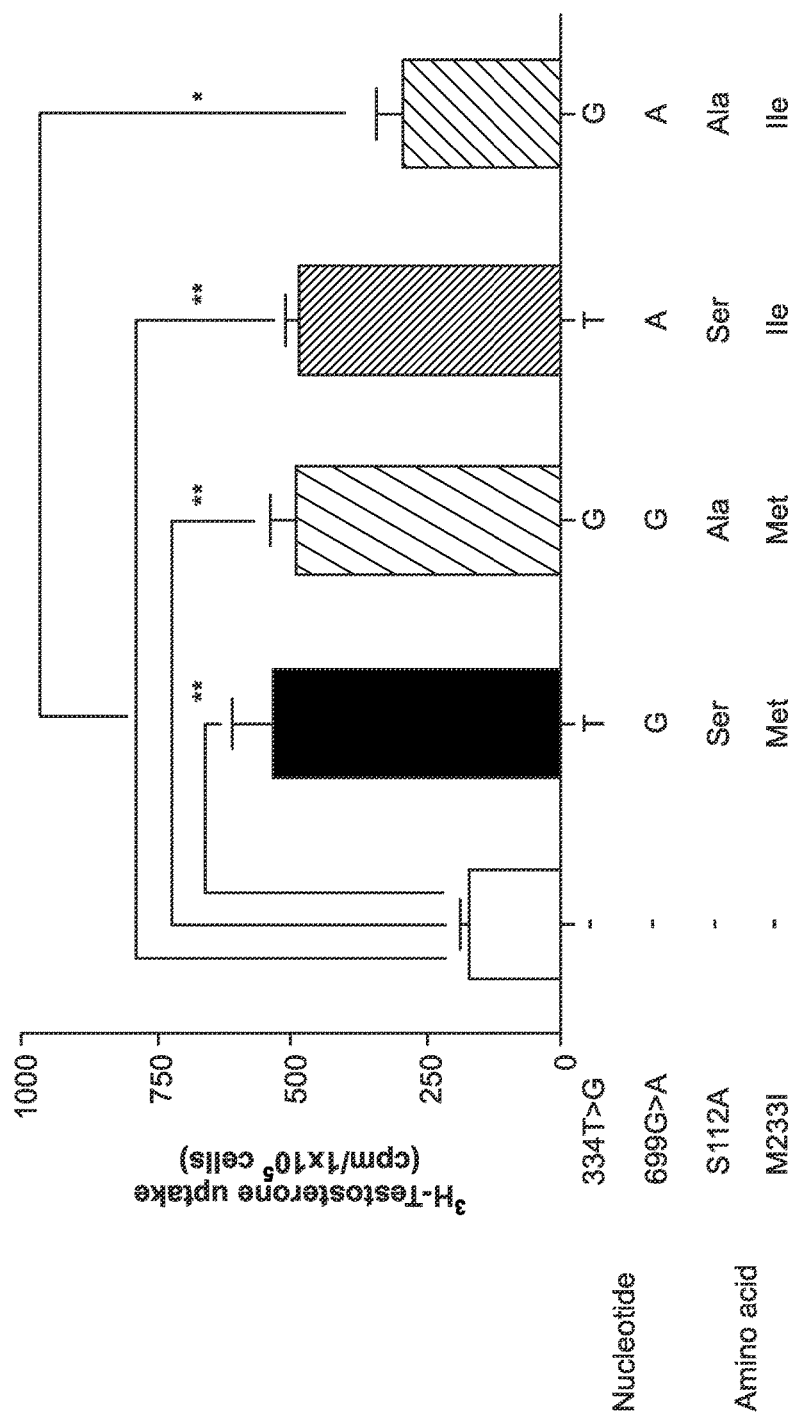
FIG. 2 depicts the influence of SLCO1B3 polymorphism on testosterone transport by Cos-7 transfected with vectors containing SLCO1B3 WT and single/double mutants. Error bars represent the SEM. **, $p<0.01$ (vector control vs WT, 334G or 699A) and *, $p<0.05$ (334G/699A vs WT); differences were analyzed by the Tukey's multiple comparison test.

The effect of transfection of Cos-7 cells with WT and variants of SLCO1B3 on testosterone uptake is shown in FIG. 2. Accumulation of testosterone was markedly induced by transfection with WT SLCO1B3 TG or variant genotypes GG and TA, with no significant differences among them. However, testosterone uptake by the SLCO1B3 GA was similar to vector control cells, thus providing evidence that while both SLCO1B3 WT and single variants actively transport testosterone into the cell, the double mutant lost most of this capability.

Expression of OATP1B3 Protein in Prostatic Tissue

Figure 3:
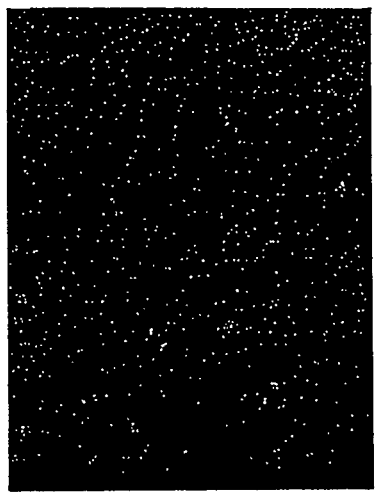
FIG. 3 depicts the immunofluorescent localization of OATP1B3. Absent to very faint immunoreactivity was observed in normal tissue and benign prostatic hyperplasia (BPH), while in prostatic cancer the immunoreactivity was strongly increased (Original magnification ×200).
Figure 3:
Figure 3:
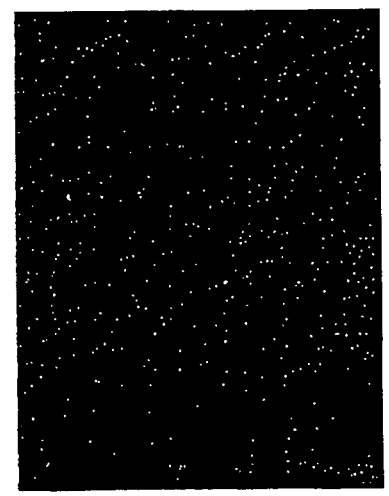

As shown in FIG. 3, the expression of OATP1B3 protein in tissues from normal prostate of BPH was almost absent, while it was markedly over-expressed in all prostate cancer tissue samples examined. The distribution of the OATP1B3 protein on the cell membrane was evidenced by the peripheral staining of the cells (FIG. 3).

Survival Analysis

Statistical analysis of the genotype prevalence did not show significant differences between patients and healthy volunteers, nor were differences observed in the frequencies of the SLCO1B3 genotypes relative to Gleason scores (p=0.31) or age at diagnosis (p=0.42) in men with prostate cancer (Table 6). Odd ratios of SLCO1B3 haplotypes for prostate cancer patients versus healthy controls crosses 1.0, thus suggesting the lack of association between SLCO1B3 polymorphisms and the development of prostate cancer in Caucasian patients (Table 6).

TABLE 6

Associations of SLCO1B3 haplotypes with selected clinical characteristics and risk of prostate cancer for Caucasian prostatic cancer patients and healthy subjects

| | TT/GG | TG/GA | GG/AA | P |
|---|---|---|---|---|
| Age at diagnosis | | | | 0.42 |
| <49 | 0 | 4 | 15 | |
| 50-59 | 4 | 10 | 43 | |
| 60-69 | 7 | 13 | 58 | |
| >70 | 2 | 5 | 19 | |
| Gleason score[a] | | | | 0.31 |
| 2-6 | 1 | 4 | 19 | |
| 7 | 5 | 6 | 38 | |
| 8-10 | 6 | 19 | 68 | |
| unknown | 1 | 3 | 10 | |
| Controls (n = 131)[b] | 9 | 26 | 96 | |

TABLE 6-continued

Associations of SLCO1B3 haplotypes with selected clinical characteristics and risk of prostate cancer for Caucasian prostatic cancer patients and healthy subjects

|  | TT/GG | TG/GA | GG/AA | P |
|---|---|---|---|---|
| Prostatic cancer (n = 180) | 13 | 32 | 13 | |
| OR (95% CI)[c] | 1 | 1.17 (0.43-3.17) | 1.03 (0.42-2.50) | 0.75[d] 0.95[e] |

Figure 4:
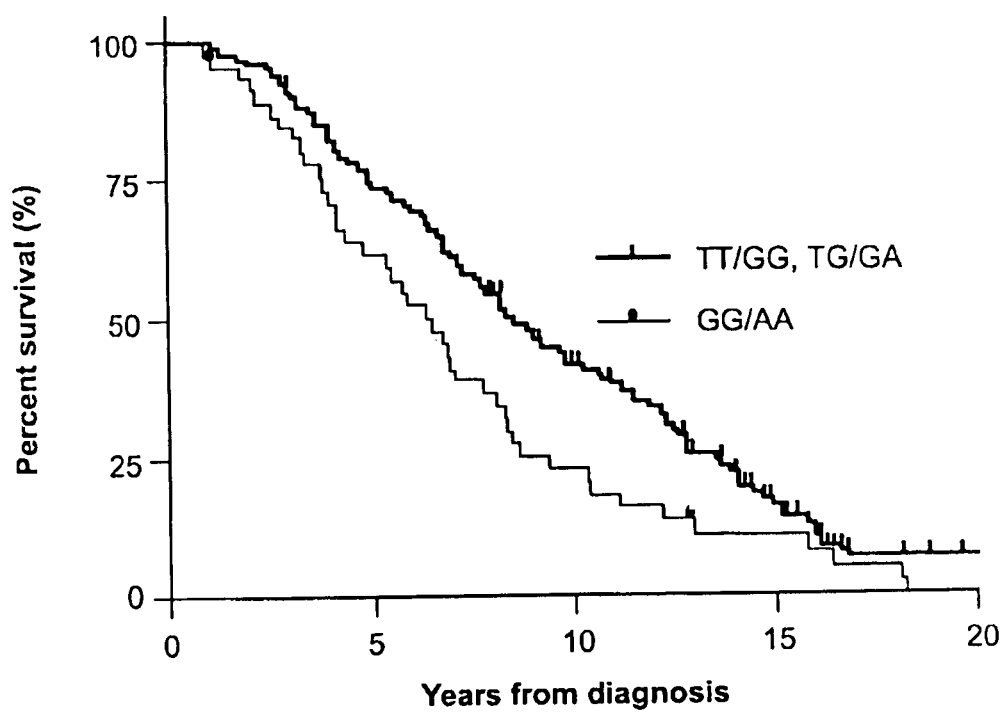
FIG. 4 depicts Kaplan-Meier survival curves in Caucasian prostatic cancer patients grouped by SLCO1B3 haplotypes (variant GG/AA vs. WT TT/GG and heterozygous TG/GA).

[a]Mildly aggressive (2-6), moderately aggressive (7) or highly aggressive (8-10)
[b]Healthy American Caucasian. Genotype frequencies are similar to previously published Caucasian controls (p = 0.34) (18).
[c]Odds ratio (OR) and 95% confidence interval (CI) of prostatic cancer vs. controls
[d]TG/GA vs. TT/GG
[e]GG/AA vs. TT/GG Since the 334T>G and 699G>A polymorphisms are in linkage disequilibrium, we used the 334T>G as the tagging SNP for the correlation of genotype with clinical outcome of patients, as shown in FIG. 4. Overall, the estimated median survival for all patients was 8.0 years (95% confidence interval [CI] 6.8 to 8.8), but the median survival for the 45 patients with both the WT TT/GG or TG/GA haplotypes was 6.4 years (95% CI 4.1 to 8.1), compared to 8.5 years (95% CI 7.2 to 10.2) for 135 patients with the GG/AA variant haplotype, the survival between the two groups being significantly different by logrank test (p=0.020, HR 1.57; 95% CI 1.11 to 2.24). The estimated survival probability at ten years was 23% (95% CI, 13% to 37%) in TT/GG or TG/GA haplotypes, and 42% (95% CI, 34% to 50%) in patients carrying the GG/AA haplotype, the difference being statistically significant (p=0.023 by the permutation test). These results suggest that survival was significantly longer for subjects with double variant haplotype.

Cells transfected with WT (334T/699G) SLCO1B3, or with a vector containing either the 334G or 699A variants, actively transported testosterone, while its uptake was impaired in cells transfected with a gene carrying both 334G and 699A SNPs. Prostatic cancer over-expresses OATP1B3 compared to normal or benign hyperplastic tissue; patients with SLCO1B3 334GG/699AA haplotype, showed longer median survival (8.5 vs. 6.4 years, p=0.020) and improved survival probability at 10 years (42 vs. 23%, p<0.023) than patients carrying TT/AA and TG/GA haplotypes.

Accordingly, the common SLCO1B3 GG/AA haplotype is associated with impaired testosterone transport and improved survival in patients with prostatic cancer.

Conclusion

This example provides evidence that testosterone uptake by cells occurs via OATP1B3 and its presence increases from undetectable levels in normal prostatic tissue and benign hyperplasia to marked expression in prostatic cancer. This example also demonstrates that the capability of testosterone transport by OATP1B3 is dependent on its genotype, the WT being most active and the variant haplotype 334GG/699AA being less efficient. Thus, OATP1B3 plays a key role in prostate cancer biology. As a confirmation of the preclinical data described herein, the SLCO1B3 double variant GG/AA haplotype was also associated with better survival of patients with prostatic cancer.

The results of this example are consistent with the research field on the genetics of enzymes involved in steroid hormone biosynthesis, including CYP17, (9, 28) CYP3A4, (29) CYP11, (30) and CYP19, (10) which were reported to be associated with the risk of developing prostate cancer or with its clinical outcome. (31) However, the role of transporters of steroid hormones was not addressed in detail previously, although it is well documented that members of the OATP/SLCO family may transport steroid hormones in normal tissues, (11)'(32)'(33) and that OATP1B3 is expressed in cancer cells derived from gastric, colon, pancreatic, lung, and breast tumors. (11)

Indeed, the transfection of Cos-7 cells with a vector carrying the 334G/699A alleles was associated with a significantly reduced ability of cells to uptake testosterone, compared to the WT vector carrying the wild-type 334T/699G haplotype.

The data of the present example demonstrate that patients with androgen-independent prostatic cancer bearing the GG/AA genotype had a significantly longer survival when compared to subjects carrying GG/AA or TG/GA genotypes.

Since the WT allele of OATP1B3 is more active than the variant allele in mediating intracellular transport of testosterone, the enhanced uptake of androgens in patients may shorten the time to androgen independence. An analysis of SLCO1B3 genotype in 80 patients shows that the time to first PSA rise from androgen deprivation therapy, which is indicative of the androgen-independent phenotype, (41) is significantly shorter with the WT TT/GG haplotype as compared to the variant GG/AA haplotype Collectively, these data indicate that OATP plays a direct role in the development of androgen-independent disease, and is involved in the failure of androgen-deprivation therapy.

In summary, this example demonstrates the important functional and biological role of OATP1B3 in prostate cancer and its significant association with survival of patients with androgen-independent disease. Therefore, SLCO1B3 genotyping may be become a useful tool for the stratification of prostatic cancer patients and for treatment decision-making. The effect on survival of the variant haplotype should be further evaluated in a larger sample size or in a population where its prevalence is higher than Caucasian, such as among African Americans, thus explaining, at least in part, the ethnic difference in prostate cancer outcome.

REFERENCES

The following specific references, also incorporated by reference, are indicated in the examples and discussion above by a number in parentheses.

1. Haiman C A, Stampfer M J, Giovannucci E, et al. The relationship between a polymorphism in CYP17 with plasma hormone levels and prostate cancer. Cancer Epidemiol Biomarkers Prev 2001; 10: 743-8.
2. Imamoto T, Suzuki H, Akakura K, et al. Pretreatment serum level of testosterone as a prognostic factor in Japanese men with hormonally treated stage D2 prostate cancer. Endocr J 2001; 48: 573-8.
3. Kakinuma H, Tsuchiya N, Habuchi T, et al. Serum sex steroid hormone levels and polymorphisms of CYP17 and SRD5A2: implication for prostate cancer risk. Prostate Cancer Prostatic Dis 2004; 7: 333-7.
4. Kerb R. Implications of genetic polymorphisms in drug transporters for pharmacotherapy. Cancer Lett 2006; 234: 4-33.
5. Ross R, Bernstein L, Judd H, Hanisch R, Pike M, Henderson B. Serum testosterone levels in healthy young black and white men. J Natl Cancer Inst 1986; 76: 45-8.
6. Soloway M S, Ishikawa S, van der Zwaag R, Todd B. Prognostic factors in patients with advanced prostate cancer. Urology 1989; 33: 53-6.

7. Titus M A, Schell M J, Lih F B, Tomer K B, Mohler J L. Testosterone and dihydrotestosterone tissue levels in recurrent prostate cancer. Clin Cancer Res 2005; 11: 4653-7.
8. Vatten L J, Ursin G, Ross R K, et al. Androgens in serum and the risk of prostate cancer: a nested case-control study from the Janus serum bank in Norway. Cancer Epidemiol Biomarkers Prev 1997; 6: 967-9.
9. Ntais C, Polycarpou A, Ioannidis J P. Association of the CYP17 gene polymorphism with the risk of prostate cancer: a meta-analysis. Cancer Epidemiol Biomarkers Prev 2003; 12: 120-6.
10. Tsuchiya N, Wang L, Suzuki H, et al. Impact of IGF-I and CYP19 gene polymorphisms on the survival of patients with metastatic prostate cancer. J Clin Oncol 2006; 24: 1982-9.
11. Abe T, Unno M, Onogawa T, et al. LST-2, a human liver-specific organic anion transporter, determines methotrexate sensitivity in gastrointestinal cancers. Gastroenterology 2001; 120: 1689-99.
12. Cui Y, Konig J, Nies A T, et al. Detection of the human organic anion transporters SLC21A6 (OATP2) and SLC21A8 (OATP8) in liver and hepatocellular carcinoma. Lab Invest 2003; 83: 527-38.
13. Konig J, Cui Y, Nies A T, Keppler D. Localization and genomic organization of a new hepatocellular organic anion transporting polypeptide. J Biol Chem 2000; 275: 23161-8.
14. Konig J, Cui Y, Nies A T, Keppler D. A novel human organic anion transporting polypeptide localized to the basolateral hepatocyte membrane. Am J Physiol Gastrointest Liver Physiol 2000; 278: G156-64.
15. Sekine T, Miyazaki H, Endou H. Molecular physiology of renal organic anion transporters. Am J Physiol Renal Physiol 2006; 290: F251-61.
16. Smith N F, Figg W D, Sparreboom A. Role of the liver-specific transporters OATP1B1 and OATP in governing drug elimination. Expert Opin Drug Metab Toxicol 2005; 1: 429-45.
17. Letschert K, Keppler D, Konig J. Mutations in the SLCO1B3 gene affecting the substrate specificity of the hepatocellular uptake transporter OATP1B3 (OATP8). Pharmacogenetics 2004; 14: 441-52.
18. Smith N F, Marsh S, Scott-Horton T J, et al. Variants in the SLCO1B3 gene: interethnic distribution and association with paclitaxel pharmacokinetics. Clin Pharmacol Ther 2007; 81: 76-82.
19. Tsujimoto M, Hirata S, Dan Y, Ohtani H, Sawada Y. Polymorphisms and linkage disequilibrium of the OATP8 (OATP1B3) gene in Japanese subjects. Drug Metab Pharmacokinet 2006; 21: 165-9.
20. Konig J, Seithel A, Gradhand U, Fromm M F. Pharmacogenomics of human OATP transporters. Naunyn Schmiedebergs Arch Pharmacol 2006; 372: 432-43.
21. Figg W D, Liu Y, Arlen P, et al. A randomized, phase II trial of ketoconazole plus alendronate versus ketoconazole alone in patients with androgen independent prostate cancer and bone metastases. J Urol 2005; 173: 790-6.
22. Bowden C J, Figg W D, Dawson N A, et al. A phase I/II study of continuous infusion suramin in patients with hormone-refractory prostate cancer: toxicity and response. Cancer Chemother Pharmacol 1996; 39: 1-8.
23. Dawson N, Figg W D, Brawley O W, et al. Phase II study of suramin plus aminoglutethimide in two cohorts of patients with androgen-independent prostate cancer: simultaneous antiandrogen withdrawal and prior antiandrogen withdrawal. Clin Cancer Res 1998; 4: 37-44.
24. Dawson N A, Figg W D, Cooper M R, et al. Phase II trial of suramin, leuprolide, and flutamide in previously untreated metastatic prostate cancer. J Clin Oncol 1997; 15: 1470-7.
25. Dahut W L, Gulley J L, Arlen P M, et al. Randomized phase II trial of docetaxel plus thalidomide in androgen-independent prostate cancer. J Clin Oncol 2004; 22: 2532-9.
26. Figg W D, Dahut W, Duray P, et al. A randomized phase II trial of thalidomide, an angiogenesis inhibitor, in patients with androgen-independent prostate cancer. Clin Cancer Res 2001; 7: 1888-93.
27. Efron B, Tibshirani R J. An Introduction to the Bootstrap. New York: Chapman & Hall; 1993.
28. Vesovic Z, Herkommer K, Vogel W, Paiss T, Maier C. Role of a CYP17 promoter polymorphism for familial prostate cancer risk in Germany. Anticancer Res 2005; 25: 1303-7.
29. Powell I J, Zhou J, Sun Y, et al. CYP3A4 genetic variant and disease-free survival among white and black men after radical prostatectomy. J Urol 2004; 172: 1848-52.
30. Cicek M S, Liu X, Casey G, Witte J S. Role of androgen metabolism genes CYP1B1, PSA/KLK3, and CYP11 alpha in prostate cancer risk and aggressiveness. Cancer Epidemiol Biomarkers Prev 2005; 14: 2173-7.
31. Gsur A, Feik E, Madersbacher S. Genetic polymorphisms and prostate cancer risk. World J Urol 2004; 21: 414-23.
32. Keppler D, Konig J, Cui Y. The human hepatocyte-specific organic anion transporter encoded by the SLC21A8 gene. Gastroenterology 2002; 122: 1545-6; author reply 6.
33. Cui Y, Konig J, Leier I, Buchholz U, Keppler D. Hepatic uptake of bilirubin and its conjugates by the human organic anion transporter SLC21A6. J Biol Chem 2001; 276: 9626-30.
34. Isern J, Hagenbuch B, Stieger B, Meier P J, Meseguer A. Functional analysis and androgen-regulated expression of mouse organic anion transporting polypeptide 1 (Oatp1) in the kidney. Biochim Biophys Acta 2001; 1518: 73-8.
35. Lu R, Kanai N, Bao Y, Wolkoff A W, Schuster V L. Regulation of renal oatp mRNA expression by testosterone. Am J Physiol 1996; 270: F332-7.
36. Roche P J, Hoare S A, Parker M G. A consensus DNA-binding site for the androgen receptor. Mol Endocrinol 1992; 6: 2229-35.
37. Sharifi N, Gulley J L, Dahut W L. Androgen deprivation therapy for prostate cancer. Jama 2005; 294: 238-44.
38. Mostaghel E A, Montgomery R B, Lin D W. The basic biochemistry and molecular events of hormone therapy. Curr Urol Rep 2007; 8: 224-32.
39. Gregory C W, Johnson R T, Jr., Mohler J L, French F S, Wilson E M. Androgen receptor stabilization in recurrent prostate cancer is associated with hypersensitivity to low androgen. Cancer Res 2001; 61: 2892-8.
40. Stanbrough M, Bubley G J, Ross K, et al. Increased expression of genes converting adrenal androgens to testosterone in androgen-independent prostate cancer. Cancer Res 2006; 66: 2815-25.
41. Sharifi N, Dahut W L, Steinberg S M, et al. A retrospective study of the time to clinical endpoints for advanced prostate cancer. BJU Int 2005; 96: 985-9.

What is claimed is:

1. A method of treating a subject having prostate cancer comprising
   determining a SLCO1B3 genotype status of a subject having prostate cancer, wherein a homozygous 334GG and/or 699AA SLCO1B3 genotype is indicative of a subject that will respond to androgen-deprivation therapy, and wild-type SLCO1B3 genotype is indicative of a patient that is unresponsive to androgen-deprivation therapy; and treating the subject having wild-type SLCO1B3 genotype by discontinuing androgen-deprivation therapy and administering a therapeutically effective amount of an anti-neoplastic agent to the subject, thereby improving survival of the subject having wild-type SLCO1B3 genotype.

2. The method of claim 1, wherein the anti-neoplastic agent is selected from one or more of docetaxel, cisplatin, cyclophosphamide, doxorubicin, prednisone, 5-FU, trastuzumab, 3G4 travacin, gemcitabine, estramustine, carboplatin, mitomycin, capecitabine, irinotecan, topotecan, vinorelbine, ifosamide, epirubicin, imatinib, gefitinib, erlotinib, cetuximab, bevacizumab, thalidomide, or radiation.

3. The method of claim 1, wherein the anti-neoplastic agent is docetaxel.

* * * * *

SEQUENCE LISTING

<160> NUMBER OF SEQ ID NOS: 22

<210> SEQ ID NO 1
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 1
ccttcacagt taaattacat ggtc                                          24

<210> SEQ ID NO 2
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 2
tattcatttc atataaaact gtatacc                                       27

<210> SEQ ID NO 3
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 3
gggcatattt gcattcattt ggg                                           23

<210> SEQ ID NO 4
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 4
catgataaat aaagaaatac atgatg                                        26

<210> SEQ ID NO 5
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 5
cactaagtca tatcaacata attttg                                        26

<210> SEQ ID NO 6
<211> LENGTH: 23
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic primer"

<400> SEQUENCE: 6
gcatacctat aggtattcct ctc                                          23

<210> SEQ ID NO 7
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 7
tgggaactgg aagtattttg acatctttac cacatttctt catg                   44

<210> SEQ ID NO 8
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 8
catgaagaaa tgtggtaaag atgtcaaaat acttccagtt ccca                   44

<210> SEQ ID NO 9
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 9
tccttgtatt taggtaacgt acag                                         24

<210> SEQ ID NO 10
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 10
tcaagtttgg ttattttgga tcaag                                        25

<210> SEQ ID NO 11
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 11
gatctaccct tgaaataata atgtc                                        25

<210> SEQ ID NO 12
```

```
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 12
gtaaaagcaa agtataaata ggagc                                          25

<210> SEQ ID NO 13
<211> LENGTH: 26
<212> TYPE: DNA
<213> ORGANISM: Artificial Sequence
<220> FEATURE:
<221> source
<223> OTHER INFORMATION: /note="Description of Artificial Sequence:
      Synthetic primer"

<400> SEQUENCE: 13
taaaagcatg ttaaatgaaa accaag                                         26

<210> SEQ ID NO 14
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 14
aaatagtaaa caaagaacta ttgaaag                                        27

<210> SEQ ID NO 15
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 15
gggatctctg tttgctaaaa tgtacgtgga tattggatat gtag                     44

<210> SEQ ID NO 16
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 16
ctacatatcc aatatccacg tacattttag caaacagaga tccc                     44

<210> SEQ ID NO 17
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 17
```

```
atatacagaa tttcatacac taatttc                                      27
```

```
<210> SEQ ID NO 18
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 18
aattctaaga aaatgcattc tcaaag                                       26
```

```
<210> SEQ ID NO 19
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 19
tattttgcct tcactattaa gcaa                                         24
```

```
<210> SEQ ID NO 20
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 20
aatatgaatt tgagctcaaa atacag                                       26
```

```
<210> SEQ ID NO 21
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 21
ggaatgtatt catagccctg ttg                                          23
```

```
<210> SEQ ID NO 22
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 22
atgacaatgt tttacaggat cata                                         24
```